(12) United States Patent
Yonemitsu et al.

(10) Patent No.: US 8,741,639 B2
(45) Date of Patent: Jun. 3, 2014

(54) METHOD FOR PRODUCING DENDRITIC CELLS

(75) Inventors: Yoshikazu Yonemitsu, Chiba (JP); Yasuji Ueda, Ibaraki (JP); Yui Harada, Saitama (JP)

(73) Assignee: DNAVEC Corporation, Tsukuba-shi, Ibaraki (JP)

( * ) Notice: Subject to any disclaimer, the term of this patent is extended or adjusted under 35 U.S.C. 154(b) by 118 days.

(21) Appl. No.: 13/127,753

(22) PCT Filed: Nov. 13, 2009

(86) PCT No.: PCT/JP2009/069311
§ 371 (c)(1),
(2), (4) Date: Nov. 7, 2011

(87) PCT Pub. No.: WO2010/055900
PCT Pub. Date: May 20, 2010

(65) Prior Publication Data
US 2012/0040458 A1 Feb. 16, 2012

(30) Foreign Application Priority Data
Nov. 14, 2008 (JP) .................. 2008-292457

(51) Int. Cl.
*A61K 39/00* (2006.01)
*C12N 5/0784* (2010.01)

(52) U.S. Cl.
CPC ........ *C12N 5/0639* (2013.01); *C12N 2501/125* (2013.01); *C12N 2501/22* (2013.01); *C12N 2501/23* (2013.01); *A61K 39/00* (2013.01)
USPC ......................................... 435/372; 435/325

(58) Field of Classification Search
CPC ........... C12N 5/0639; C12N 2501/125; C12N 2501/22; C12N 2501/23; A61K 39/00
USPC ................................. 435/372, 325
See application file for complete search history.

(56) References Cited

U.S. PATENT DOCUMENTS

| 5,866,115 | A | 2/1999 | Kanz et al. |
| 2008/0145931 | A1 | 6/2008 | Healey et al. |
| 2010/0184214 | A1 | 7/2010 | Inoue et al. |

FOREIGN PATENT DOCUMENTS

| JP | 2005-102656 A | 4/2005 |
| JP | 2008-515439 A | 5/2008 |
| WO | WO-95/28479 A1 | 10/1995 |
| WO | WO-2006/020889 A2 | 2/2006 |
| WO | WO-2006/130651 A2 | 12/2006 |
| WO | WO 2008/143047 A1 | 11/2008 |
| WO | WO-2009/120891 A2 | 10/2009 |

OTHER PUBLICATIONS

Banchereau and Steinman "Dendritic cells and the control of immunity," *Nature* 392(6673):245-252 (1998).
Berthier et al. "A two-step culture method starting with early growth factors permits enhanced production of functional dendritic cells from murine splenocytes," *J Immunol. Methods* 239(1-2):95-107 (2000).
Fadilah et al. "Cord blood CD34+ cells cultured with FLT3L, stem cell factor, interleukin-6, and IL-3 produce CD11c+ CD1a−/c− myeloid dendritic cells," *Stem Cell. Dev.* 16(5):849-855 (2007).
Harada et al. "Cytokine-based log-scale expansion of functional human dendritic cells," The 10th Symposium on Dendritic Cells, p. 4-25, p. 187, 2008.
Knutson and Disis "Tumor antigen-specific T helper cells in cancer immunity and immunotherapy," *Cancer Immunol. Immunother.* 54(8):721-728 (2005); published online Jan. 27, 2005.
Liu et al. "Generation of functional and mature dendritic cells from cord blood and bone narrow CD34+ cells by two-step culture combined with calcium ionophore treatment," *J. Immunol. Methods.* 261(1-2):49-63 (2002).
Obermaier et al. "Development of a new protocol for 2-day generation of mature dendritic cells from human monocytes," *Biol. Proced. Online.* 59 1):197-203 (2003).
Ryu et al. "In vitro generation of functional dendritic cells from human umbilical cord blood CD34+cells by a 2-step culture method," *Int. J. Hematol.* 80(3):281-286 (2004).
Shibata et al. "Induction of efficient antitumor immunity using dendritic cells activated by recombinant Sendai virus and its modulation by exogenous IFN-βgene," *J Immunol.* 177(6):3564-3576 (2006).
Steinman "The dendritic cell system and its role in immunogenicity," *Annu. Rev. Immunol.* 9:271-296 (1991).
Uemura et al. "Fundamental research for therapy of regulating T helper type I and type II immune responses using dendritic cells," *Journal of Saitama Medical University* 33(3, 4):67-72 (2006) and English translation.
English language translation of Uemura et al. "Fundamental research for therapy of regulating T helper type I and type II immune responses using dendritic cells," *Journal of Saitama Medical University.* 33:67-72 (2006).
Yoneyama et al. "Development of immunostimulatory virotherapy using non-transmissible Sendai virus-activated dendritic cells," *Biochem. Biophys. Res. Commun.* 355(1):129-135 (2007); available online Feb. 2, 2007.
English language translation of International Search Report for International Application No. PCT/JP2009/069311, mailed Dec. 8, 2009 (2 pages).
English language translation of Written Opinion for International Application No. PCT/JP2009/069311, mailed Dec. 8, 2009 (4 pages).
English language translation of International Preliminary Report on Patentability for International Application No. PCT/JP2009/069311, report issued Jun. 21, 2011, mailed Jun. 30, 2011.

(Continued)

*Primary Examiner* — Prema Mertz
(74) *Attorney, Agent, or Firm* — Clark & Elbing LLP

(57) ABSTRACT

An objective of the present invention is to provide methods for producing dendritic cells (DCs), which comprise the step of culturing DC precursor cells in the presence of a plurality of cytokines, produced dendritic cells, and uses thereof.
The present inventors discovered that dendritic cells with a high IL-12 productivity can be obtained by culturing DC precursor cells in the presence of a plurality of cytokines, followed by about one week of culture in the presence of GM-CSF and IL-4. The present invention enables preparation of a large amount of DCs with a high IL-12 productivity from a small number of DC precursor cells, and therefore makes it easier to increase the number of DCs for administration in DC-based anti-tumor immune therapy, treatment of infections, etc. Thus, the effect of DC vaccines is expected to be enhanced.

5 Claims, 6 Drawing Sheets

(56) References Cited

OTHER PUBLICATIONS

Hieronymus et al., "Progressive and Controlled Development of Mouse Dendritic Cells from Flt3+CD11b+Progenitors In Vitro," *J. Immunol.* 174(5):2552-2562 (2005).

Paczesny et al., "Efficient Generation of CD34+ Progenitor-Derived Dendritic Cells from G-CSF-Mobilized Peripheral Mononuclear Cells Does Not Require Hematopoietic Stem Cell Enrichment," *J. Leukoc. Biol.* 81(4):957-967 (2007).

Akiyama et al., "Retroviral-Mediated IL-12 Gene Transduction into Human CD34+ Cell-Derived Dendritic Cells," *Int. J. Oncol.* 21:509-514 (2002).

Balan et al., "A Simple Two-Step Culture System for the Large-Scale Generation of Mature and Functional Dendritic Cells from Umbilical Cord Blood CD34+ Cells," *Transfusion* 49:2109-2121 (2009).

Encabo et al., "Selective Generation of Different Dendritic Cell Precursors from CD34+ Cells by Interleukin-6 and Interleukin-3," *Stem Cells* 22:725-740 (2004).

Hagihara et al., "Extensive and Long-Term Ex Vivo Production of Dendritic Cells from CD34 Positive Umbilical Cord Blood or Bone Marrow Cells by Novel Culture System Using Mouse Stroma," *J. Immunol. Methods* 253:45-55 (2001).

Harada et al., "Flt3 Ligand Promotes Myeloid Dendritic Cell Differentiation of Human Hematopoietic Progenitor Cells: Possible Application for Cancer Immunotherapy," *Int. J. Oncol.* 30:1461-1468 (2007).

Extended European Search Report issued in European Patent Application No. 09826146.4, dated Apr. 9, 2013, including Supplementary European Search Report (8 pages).

Borràs et al., "Dendritic cells can be successfully generated from CD34+ cord blood cells in the presence of autologous cord blood plasma," *Bone Marrow Transplant.* 26:371-376 (2000).

Čolić et al., "Mycophenolate mofetil inhibits differentiation, maturation and allostimulatory function of human monocyte-derived dendritic cells," *Clin Exp Immunol.* 134:63-69 (2003).

Kuwana et al., "Human circulating CD14+ monocytes as a source of progenitors that exhibit mesenchymal cell differentiation," *J Leukoc Biol.* 74:833-845 (2003).

Santiago-Schwarz et al., "Neutralization of tumor necrosis factor activity shortly after the onset of dendritic cell hematopoiesis reveals a novel mechanism for the selective expansion of the CD14-dependent dendritic cell pathway," *Blood* 92:745-755 (1998).

iDC TREATMENT GROUP  OK432 TREATMENT GROUP

METHOD FOR PRODUCING DENDRITIC CELLS

CROSS-REFERENCE TO RELATED APPLICATIONS

This application is the U.S. National Stage Application of international patent application PCT/JP2009/069311, filed Nov. 13, 2009, which claims the benefit of Japanese Patent Application No. JP 2008-292457, filed Nov. 14, 2008.

TECHNICAL FIELD

The present invention relates to methods for producing dendritic cells, produced dendritic cells, and uses thereof.

BACKGROUND ART

Dendritic cells (DCs) are antigen-presenting cells (APCs) present in peripheral blood, skin, lymphatic organs, and thymus, and are widely distributed in lymphatic and non-lymphatic tissues (see Steinman, R. M. Ann. Rev. Immunol. 9:271 (1991); Banchereau, J. B. and R. M. Steinman, Nature 392:245 (1998)). Dendritic cells have a strong antigen-presenting ability and express antigenic peptides on class I and II molecules on the dendritic cell surface, which activate CD4 and CD8 T cells, respectively. Through this activation, DCs induce an in vivo immune response against specific antigens (e.g., antigens of pathogenic microorganisms, tumor-related antigens, and transplantation antigens).

The strong ability of DCs to induce immunity is useful in immunotherapy (DC therapy) against many tumors. The present inventors have previously demonstrated that DCs stimulated with Sendai virus (SeV) have a strong anti-tumor effect in mice (S. Shibata et al., J. Immunol, 177: 3564-3576 (2006); Yoneyama, Y. et al., Biochem. Biophys. Res. Commun., 355:129-135 (2007)). The anti-tumor effect depends on the number of DCs inoculated. Clinically, the inoculated DC number is also thought to have a large influence on the therapeutic effect. However, there may be many cases where only a limited number of DC precursor cells (DC progenitors) can be collected due to a patient's condition. As a result, the therapeutic effect may become insufficient due to the insufficient number of DCs obtained. Thus, there is a demand for methods that efficiently expand limited DC precursor cells. Furthermore, to achieve an anti-cancer effect, there is a need for an efficient method for preparing DCs with high interleukin 12 (IL-12) productivity (Cancer Immunol Immunother., (2005) 54:721-728) (Japanese Patent Kohyo Publication No. (JP-A) 2008-515439 (unexamined Japanese national phase publication corresponding to a non-Japanese international publication)).

Prior art documents related to the present invention are shown below.

PRIOR-ART DOCUMENTS

Non-Patent Documents

Non-patent Document 1: Steinman, R. M., Ann. Rev. Immunol., (1991) 9: 271-296
Non-patent Document 2: Banchereau, J. B. and R. M. Steinman, Nature, (1998) 392: 245-252
Non-patent Document 3: Shibata, S. el al., J. Immunol., (2006) 177: 3564-3576
Non-patent Document 4: Yoneyama, Y. et al., Biochem. Biophys. Res. Commun., (2007) 355:129-135
Non-patent Document 5: Knutson, K. L. et al., Cancer Immunol Immunother., (2005) 54: 721-728

Patent Documents

Patent Document 1: JP-A (Kohyo) 2008-515439

DISCLOSURE OF THE INVENTION

Problems to be Solved by the Invention

The present invention was achieved in view of the above circumstances. An objective of the present invention is to provide efficient methods for producing dendritic cells having the ability to produce high levels of IL-12.

Means for Solving the Problems

Recently, the present inventors developed an efficient method for expanding DCs. However, they found that DCs prepared by this method were very poor in IL-12 productivity. This suggests the possibility that such DCs may not produce a sufficient anti-cancer effect in vivo. Dedicated studies by the present inventors led to the instant invention, which relates to efficient methods for preparing DCs with a high IL-12 productivity. The present invention relates to methods for producing dendritic cells, produced dendritic cells, uses thereof, etc. More specifically, the present invention relates to:

[1] a method for producing a dendritic cell, which comprises the steps of:
(1) culturing a dendritic cell precursor cell in the presence of:
   (a) any one of (i) to (v) selected from the group consisting of: (i) granulocyte/macrophage-colony stimulating factor (GM-CSF), (ii) interleukin 3 (IL-3), (iii) thrombopoietin (TPO), (iv) Flt-3 ligand (Flt-3L), and (v) Flt-3L, TPO, and IL-6; and
   (b) stem cell factor (SCF); and
(2) culturing the cell cultured in step (1) in the presence of GM-CSF and IL-4;

[2] the method of [1] for producing a dendritic cell, which comprises the steps of:
(1) culturing a dendritic cell precursor cell in the presence of granulocyte/macrophage-colony stimulating factor (GM-CSF) and stem cell factor (SCF); and
(2) culturing the cell cultured in step (1) in the presence of GM-CSF and IL-4;

[3] the method of [1] for producing a dendritic cell, which comprises the steps of:
(1) culturing a dendritic cell precursor cell in the presence of IL-3 and SCF; and
(2) culturing the cell cultured in step (1) in the presence of GM-CSF and IL-4;

[4] the method of [1] for producing a dendritic cell, which comprises the steps of:
(1) culturing a dendritic cell precursor cell in the presence of TPO and SCF; and
(2) culturing the cell cultured in step (1) in the presence of GM-CSF and IL-4;

[5] the method of [1] for producing a dendritic cell, which comprises the steps of:
(1) culturing a dendritic cell precursor cell in the presence of Flt-3L and SCF; and
(2) culturing the cell cultured in step (1) in the presence of GM-CSF and IL-4;

[6] the method of [1] for producing a dendritic cell, which comprises the steps of:

(1) culturing a dendritic cell precursor cell in the presence of Flt-3L, TPO, IL-6, and SCF; and
(2) culturing the cell cultured in step (1) in the presence of GM-CSF and IL-4;
[7] the method of any one of [1] to [6], wherein the dendritic cell precursor cell is a human-derived cell; and
[8] the method of [7], wherein the human-derived cell is a cord blood-derived CD34$^+$ cell.

In each of the above items that cite the same item, any combination of two or more inventions described therein is intended to be included in the generic item cited. The present specification is intended to include any components of the inventions described therein and any combinations thereof. The present specification is also intended to include inventions excluding any components of the inventions described therein, and any combinations thereof. Furthermore, when the present specification describes certain specific embodiments as being preferable, the present specification not only discloses these embodiments, but also discloses inventions excluding these embodiments from generic inventions disclosed.

Effects of the Invention

Dendritic cells have a strong ability to induce immunity. Thus, dendritic cells obtained by the methods of the present invention are useful as dendritic cell (DC) vaccines useful in immunotherapy for cancer, infections, and such. For example, in tumor immunotherapy, dendritic cells are made to present tumor antigens by mixing dendritic cells with tumor cell lysates, pulsing dendritic cells with peptides, introducing tumor antigen genes into dendritic cells, or such, and used in DC therapy against tumors. Even when the quantity of DCs collected from a patient is small, DCs sufficient enough in number to produce a therapeutic effect can be prepared by using the methods of the present invention.

BRIEF DESCRIPTION OF THE DRAWINGS

A scale of the vertical axis of the graph in FIG. 1, which is described below, indicates the following:
1.E+04, 1e4, or 1.00E+04: $1.0 \times 10^4$ (cells)
1.E+05 or 1.00E+05: $1.0 \times 10^5$ (cells)
1.E+06 or 1.00E+06: $1.0 \times 10^6$ (cells)
1.E+07 or 1.00E+07: $1.0 \times 10^7$ (cells)
1.E+08 or 1.00E+08: $1.0 \times 10^8$ (cells)
1.E+09 or 1.00E+09: $1.0 \times 10^9$ (cells)
1.E+10 or 1.00E+10: $1.0 \times 10^{10}$ (cells)
1.E+11 or 1.00E+11: $1.0 \times 10^{11}$ (cells)

Human cord blood-derived CD34$^+$ cells were cultured in culture media containing particular cytokines.

MODE FOR CARRYING OUT THE INVENTION

Figure 1:
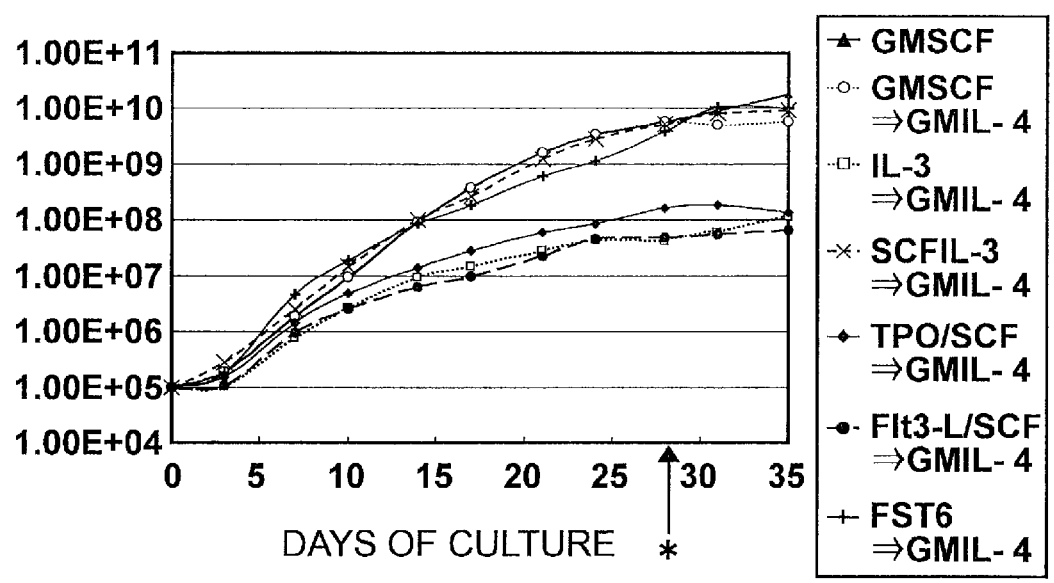
FIG. 1 shows the results of this expansion and differentiation using curve graphs. The details are as follows: Asterisk (*) indicates the time point of day 28. "GMSCF": a sample from a 35-day culture of CD34$^+$ cells under GMSCF administration group culture conditions. "GMSCF→GMIL-4": a sample from a 28-day culture of CD34$^+$ cells under GMSCF administration group culture conditions, followed by a 7-day culture under GMIL-4 administration group culture conditions. "IL-3→GMIL-4": a sample from a 28-day culture of CD34$^+$ cells under IL-3 administration group culture conditions, followed by a 7-day culture under GMIL-4 administration group culture conditions. "SCFIL-3→GMIL-4": a sample of a 28-day culture of CD34$^+$ cells under IL-3SCF administration group culture conditions, followed by a 7-day culture under GMIL-4 administration group culture conditions. "TPO/SCF→GMIL-4": a sample of a 28-day culture of CD34$^+$ cells under TPOSCF administration group culture conditions, followed by a 7-day culture under GMIL-4 administration group culture conditions. "Flt3-L/SCF→GMIL-4": a sample of a 28-day culture of CD34$^+$ cells under FS administration group culture conditions, followed by a 7-day culture under GMIL-4 administration group culture conditions. "FST6→GMIL-4": a sample of a 28-day culture of CD34$^+$ cells under FST6 administration group culture conditions, followed by a 7-day culture under GMIL-4 administration group culture conditions.

The present invention relates to methods for producing dendritic cells, which comprise the step of culturing dendritic cell precursor cells in the presence of a plurality of cytokines. More specifically, the present invention relates to methods for producing dendritic cells, which comprise the steps of:

(1) culturing dendritic cell precursor cells in the presence of stem cell factor (SCF) and a cytokine selected from the group consisting of (i) to (v) below; and (2) culturing the cells cultured in step (1) in the presence of GM-CSF and IL-4.

The groups of (i) to (v) are as follows:
(i) granulocyte/macrophage-colony stimulating factor (GM-CSF)
(ii) IL-3
(iii) TPO
(iv) Flt-3L
(v) Flt-3L, TPO, and IL-6

DC precursor cells can be efficiently expanded and/or differentiated via the above-described steps. Furthermore, DCs with a high IL-12 productivity can be efficiently produced by the steps. Herein, "in the presence of a particular cytokine" means that at least that particular cytokine is contained. Other cytokines may be contained in addition to the particular cytokine. Preferably, the particular cytokine is contained exclusively, for example, without any other cytokines. The period of culture is not limited; however, it is preferably about three to five weeks, more preferably about three to four weeks, for example, may be 15 days or more, 16 days or more, 18 days or more, 19 days or more, 20 days or more, 21 days or more, 22 days or more, 23 days or more, 24 days or more, 25 days or more, 38 days or less, 35 days or less, 30 days or less, 29 days or less, 28 days or less, 27 days or less, 26 days or less, 25 days or less, 24 days or less, 22 days or less, 21 days or less, or 20 days or less.

Herein, a dendritic cell (DC) is a cell which takes a dendritic morphology in the mature state and has the ability to activate T cells by presenting an antigen. Herein, a dendritic cell precursor cell is a cell that differentiates into DC in the presence of an appropriate cytokine (for example, G-CSF, GM-CSF, TNF-α, IL-4, IL-13, SCF (c-kit ligand), Flt-3 ligand, or a combination thereof). It is preferably is a cell that can differentiate into a dendritic cell in four weeks or less, more preferably in 20 days or less, even more preferably in 18 days or less, and still more preferably in 16 days or less. Such cells include CD34+ stem cells, hematopoietic progenitor cells, and bone marrow mononuclear cells. These cells can be prepared, for example, as a cell fraction. A cell fraction is a cell population obtained by separation (or fractionation) of cells. A cell fraction may be a composition comprising cells and a pharmaceutically acceptable carrier. Carriers include desired solutions in which viable cells can be suspended, such as physiological saline, phosphate-buffered saline (PBS), culture media, and sera.

Dendritic cells include groups of bone marrow-derived cells with dendritic morphology distributed in various tissues and organs in the body, groups of cells with dendritic morphology distributed in various organs and tissues in the body that result from in vitro differentiation using cytokines or such from bone marrow- or blood-derived stem cells and equivalent cells. Specifically, the dendritic cells include, for example, lymphocytic dendritic cells (including cells which induce Th2 or immune tolerance), bone marrow dendritic cells (generally used dendritic cells, including immature and mature dendritic cells), Langerhans cells (dendritic cells important as antigen-presenting cells in the skin), interdigitating cells (distributed in the lymph nodes and spleen T cell region, and believed to function in antigen presentation to T cells), and follicular dendritic cells (important as antigen-presenting cells for B cells; the cells present antigens to B cells by presenting antigen-antibody complexes or antigen-complement complexes on the surface via the antibody receptor or the complement receptor). Preferably, the dendritic cells highly express MHC class I and class II, and more preferably express CD11c. DCs or DC precursor cells derived from cells collected from bone marrow, cord blood, or peripheral blood are more preferably used in the present invention. DC precursor cells include, for example, CD34-positive cells.

The species from which DCs are derived are not particularly limited, and may be mammals, including primates such as humans and monkeys, rodents such as mice and rats, as well as rabbits, bovines, and goats. A dendritic cell may also be a cell with dendritic morphology and that is positive for two or more surface markers selected from the group consisting of CD11c, HLA-class II (HLA-DR, -DP, or -DQ), CD40, and CD1a. The dendritic cell of the present invention is more preferably an HLA-class II$^+$ and CD11c$^+$ cell, even more preferably, a CD1a$^+$, HLA-class II$^+$, and CD11c$^+$ cell that is negative in lineage markers (Lin$^-$), i.e., that is devoid of the expression of T cell marker (CD3), B cell markers (CD19, CD20), NK cell marker (CD56), neutrophil marker (CD15), and monocyte marker (CD14). When the cells are myeloid dendritic cells (myeloid DCs), they preferably also express CD11b. For example, CD11b$^+$, CD11c$^+$ cells are included in the DCs of the present invention. When the cells are lymphoid dendritic cells (lymphoid DC), they may also express CD8.

In addition, the dendritic cells of the present invention include both mature and immature dendritic cells. "Immature dendritic cells" refers to dendritic cells having a significantly low T cell-activating ability as compared with a mature state. Specifically, the immature dendritic cells may have an antigen-presenting ability that is lower than ½, preferably lower than ¼ of that of dendritic cells in which maturation had been induced by adding LPS (1 μg/ml) and culturing for two days. The antigen-presenting ability can be quantified, for example, using the allo T cell-activating ability (mixed lymphocyte test: allo T cells and dendritic cells are co-cultured at a T cell:dendritic cell ratio of 1:10, or preferably at varied ratios; 3H-thymidine is added eight hours before terminating cultivation, and the T cell growth capacity is assessed based on the amount of $^3$H-thymidine incorporated into the DNA of the T cells (see Gene Therapy 7; 249-254 (2000)). Alternatively, it can be assessed by testing the ability to induce specific cytotoxic T cells (CTLs) using a peptide, in which a known class I-restricted peptide of a certain antigen is added to dendritic cells; the dendritic cells are co-cultured with T cells obtained from peripheral blood of the same healthy donor from whom the dendritic cells had been collected (with 25 U/ml or preferably 100 U/ml of IL-2 on day 3 or later). The T cells are preferably stimulated with dendritic cells three times during 21 days, more preferably stimulated with dendritic cells twice during 14 days. The resulting effector cells are co-cultured for four hours with $^{51}$Cr-labeled target cells (peptide-restricted class I positive tumor cells) at a ratio of 100:1 to 2.5:1 (100:1, 50:1, 25:1, 20:1, 12.5:1, 10:1, 5:1, or 2.5:1), preferably at a ratio of 10:1; and $^{51}$Cr released from the target cells is quantified (see Arch Dermatol Res 292:325-332 (2000)). Furthermore, the immature dendritic cells preferably have phagocytic ability for antigens, and more preferably show low (for example, significantly low as compared to mature DCs induced by LPS as described above) or negative expression of receptors that induce the costimulation for T cell activation. On the other hand, "mature dendritic cells" refers to dendritic cells that have a significantly strong antigen-presenting ability for T cell activation or the like as compared with the immature state. Specifically, the mature dendritic cells may have an antigen-presenting ability that is half or stronger, preferably equivalent to or stronger than the antigen-presenting ability of dendritic cells in which maturation has been induced by adding LPS (1 μg/ml) and culturing for two days. Furthermore, the mature dendritic cells preferably have weak or no phagocytic ability for antigen, and more preferably are positive for the expression of receptors that induce the costimulation for T cell activation. The activation of dendritic cells refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli.

Mature human dendritic cells are cells that are positive for the expression of CD40, CD80, CD86, and HLA-class II. An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive.

As described above, immature dendritic cells generally have a high phagocytic ability. When dendritic cells are added with LPS (1 μg/ml) and cultured for two days, they become activated and their phagocytic ability is reduced. The phagocytic ability can be detected by measuring the amount of small molecules taken up into dendritic cells or the proportion of uptaking cells. The phagocytic ability is preferably determined by the amount of small molecules taken up into dendritic cells. For example, using colored beads with a diameter of about 1 μm, the uptake of beads into dendritic cells can be measured. Quantitation is performed by subtracting the positive background at 4° C. A high phagocytic ability indicates an ability wherein the amount of small molecules taken up into dendritic cells is four times or more, more preferably five times or more, and even more preferably six times or more than that taken up into dendritic cells stimulated with LPS (1 μg/ml) for two days as described above. Alternatively, the proportion of cells taking up small molecules is twice or more, and more preferably three times or more. A low phagocytic ability is indicated when the amount of small molecules taken up into dendritic cells is less than four times, more preferably less than twice, and more preferably less than 1.5 times to that taken up into dendritic cells stimulated with LPS (1 μg/ml) for two days. Alternatively, when measured as the proportion of cells that take up small molecules, the proportion is less than twice, and more preferably less than 1.5 times.

Discrimination of mature dendritic cells is routinely performed by those skilled in the art, and the respective markers described above and methods for measuring their expression are also well known to those skilled in the art. For example, CD11c is an adhesion glycoprotein of about 150 kD (p150, integrin a chain). CD11c binds to CD18 to form a CD11c/CD18 complex, which is capable of binding to fibrinogen and has been reported to function as a receptor for iC3b and ICAM-1. In addition, it has been reported that CD11c/CD18 can function as an adhesion molecule that binds to receptors on stimulated epithelia (Knapp, W. et al., eds., 1989, Leucocyte Typing IV: White Cell Differentiation Antigens, Oxford University Press, New York; Barclay, N. A. et al., eds., 1993, The Leucocyte Antigen Facts Book, CD11 Section, Academic Press Inc., San Diego, Calif., p. 124; Stacker, S. A. and T. A. Springer, 1991, J. Immunol. 146:648).

CD1a is a polypeptide of about 49 kD, which binds to β2 microglobulin. CD1a is structurally similar to an MHC class I antigen and is assumed to function in antigen presentation (Knapp, W. et al., eds., 1989, Leucocyte Typing IV: White Cell Differentiation Antigens, Oxford University Press, New York; Schlossman, S. et al., eds., 1995, Leucocyte Typing V: White Cell Differentiation Antigens. Oxford University Press, New York; Hanau, D. et al., 1990, J. Investigative Dermatol. 95: 503; Calabi, F. and A. Bradbury., 1991, Tissue Antigens 37: 1).

CD11b is also referred to as integrin αM chain, Mac-1, CR3, iC3bR (complement receptor type 3), or Mo 1, and is a type I transmembrane glycoprotein with a molecular weight of about 165 to 170. CD11b functions as a receptor for complement (iC3b), fibrinogen, and coagulation factor X, and is involved in phagocytosis (Todd R. F. et al. J. Immunol., 126, 1435-1442 (1981); Leong A. S. Y. Appl. Immunohistochem. Surg. Pathol., 120-128 (1993); Todd R. F. et al. Hybridoma, 1, 329-337 (1982); Cobbold S. et al. Leucocyte Typing III, 788-803 (1987); Keizer G. et al. Eur. J. Immunol., 15, 1142-1148. (1985); Laffon A. et al. J. Clin. Invest., 88, 546-552 (1991); Acevedo A. et al. J. Invest. Dermatol., 97, 659-666 (1991)).

CD11c (integrin αX subunit, or p150 leukocyte surface antigen) is a molecule of the integrin family, and like other leukocyte integrins (CD11a, CD11b, and CD11d), it binds to the integrin β2 subunit (CD 18) non-covalently. CD11c is a transmembrane glycoprotein with a molecular weight of 145 to 150 kDa, and is well known as a dendritic cell marker (Molica S. et al. Blood, 81, 2466 (1993); Van der Vieren M. et al. Immunity, 3, 683-690 (1995); Hogg N. et al. Leucocyte Typing III, 576-602 (1987)).

CD14 is a glycosylphosphatidylinositol (GPI)-anchored single-chain glycoprotein of 53 to 55 kD expressed in dendritic reticulum cells and some types of Langerhans cells. CD14 was identified as a surface receptor having high affinity to a complex of LPS and serum LPS-binding protein (LPB) (McMichael, A. J. et al., eds., 1987, Leucocyte Typing III: White Cell Differentiation Antigens, Oxford University Press, New York; Knapp, W. et al., eds., 1989, Leucocyte Typing IV: White Cell Differentiation Antigens, Oxford University Press, New York; Schlossman, S. et al., eds., 1995, Leucocyte Typing V: White Cell Differentiation Antigens. Oxford University Press, New York; Wright, S. D. et al., 1990, Science 249:1434).

CD40 is a type I integral membrane protein of 45 to 48 kD (type I integral membrane glycoprotein). Anti-CD40 antibody is frequently used as a cell marker (Schlossman, S. et al., cds., 1995, Leucocyte Typing V: White Cell Differentiation Antigens. Oxford University Press, New York; Galy, A. H. M.; and H. Spits, 1992, J. Immunol. 149: 775; Clark, E. A. and J. A. Ledbetter, 1986, Proc. Natl. Acad. Sci. 83: 4494; Itoh, H. et al., 1991, Cell 66: 233; Barclay, N. A. et al., 1993, The Leucocyte Antigen Facts Book., Academic Press).

CD80 is a transmembrane glycoprotein of about 60 kD, and is a member of the Ig supergene family. CD80 is a ligand for CD28 and CD 152 (CTLA-4) expressed in T cells (Schlossman, S. et al., eds., 1995, Leucocyte Typing V: White Cell Differentiation Antigens. Oxford University Press, New York; Schwarts, R. H., 1992, Cell 71: 1065; Azuma, M. et al., 1993, J. Exp. Med. 177: 845; Koulova, L. et al., 1991, J. Exp. Med. 173: 759; Freeman, G. J. et al., 1998, J. Immunol. 161: 2708; Behrens, L. et al., 1998, J. Immunol., 161(11):5943; Guesdon, J.-L. et al., 1979, J. Histochem. Cytochem. 27: 1131-1139).

CD83 is a transmembrane protein of about 45 kD, and is a member of the Ig superfamily. CD83 has a short extracellular domain of V-type Ig and a C-terminal cytoplasmic tail. CD83 is mainly expressed in follicular dendritic cells, circulating dendritic cells, interdigitating dendritic cells in lymphatic tissues, in vitro-produced dendritic cells, and dendritic cells of the thymus (Zhou, L-J., and T. F. Tedder, 1995, J. Immunol. 154. 3821; Zhou, L-J. et al., 1992, J. Immunol. 149: 735; Summers, K. L. et al., 1995, Clin Exp. Immunol. 100:81; Weissman, D. et al., 1995, Proc. Natl. Acad. Sci USA. 92: 826; Hart, D. N. J., 1997, Blood 90: 3245).

CD86 (B70/B7-2) is a cell surface protein of about 75 kD, which is a second ligand for CD28 and CTLA-4 and plays an important role in costimulation of T cells in early immune response (Azuma M. et al., 1993, Nature 366: 76; Nozawa Y. et al., 1993, J. Pathology 169: 309; Engle, P. et al. 1994, Blood 84: 1402; Engel, P. et al., CD86 Workshop Report. In: Leukocyte Typing V. Schlossman, S. F. et al. eds., 1994, Oxford University Press; Yang, X. F. et al., 1994, Upregulation of CD86 antigen on TPA stimulated U937 cells, 1994, (abstract). American Society of Hematology, Nashville, Tenn.; Guesdon, J.-L. et al., 1979, J. Histochem. Cytochem. 27: 1131-1139).

CCR7 is also called BLR-2, EBI-1, and CMKBR7, which is a seven-transmembrane G protein-coupled receptor, and is a receptor of the CC chemokines, MIP-3β/Exodus 3/ELC/CCL19 and 6Ckine/Exodus 2/SLC/TCA4/CCL21 (Sallusto, F. et al., 1999, Nature 401:708-12; Lipp, M. et al., 2000, Curr. Top. Microbiol. Immunol. 251:173-9; Birkenbach, M. et al., 1993, J. Virol. 67:2209-20; Schweickart, V. L. et al., 1994, Genomics 23:643-50; Burgstahler, R. et al., 1995, Biochem. Biophys. Res. Commun. 215:737-43; Yoshida, R. et al., 1997, J. Biol. Chem. 272:13803-9; Yoshida, R. et al., 1998, J. Biol. Chem. 273:7118-22; Yoshida, R. et al., 1998, Int. Immunol, 10:901-10; Kim, C. H. et al., 1998, J. Immunol. 161:2580-5; Yanagihara, S. et al., 1998, J. Immunol 161:3096-102).

DR, DP, and DQ exist as HLA-class II, and can be collectively detected using antibodies that bind to all of these (Pawelec, G. et al., 1985, Iluman Immunology 12:165; Ziegler, A. et al., 1986, Immunobiol. 171:77). HLA-DR is one of the human MHC class II antigens, which is a transmembrane glycoprotein consisting of an α chain (36 kDa) and a β subunit (27 kDa). In epidermal Langerhans cells, it is co-expressed with CD1a antigen. CD1a plays a principal role in cell interaction for antigen presentation (Barclay, N. A. et al., 1993, The Leucocyte Antigen Facts Book. p. 376. Academic Press).

Dendritic cells of humans and nonhuman mammals can be specified using products of the above-described marker genes and homologous genes thereof as an indicator. Antibodies for such markers are available, for example, from BD Biosciences (BD PharMingen), and detailed information is available at the company website or its distributor websites.

For dendritic cell markers, also see the references by Kiertscher et al. and Oehler et al. (Kiertscher S M, Roth M D, Human CD14$^+$ leukocytes acquire the phenotype and function of antigen-presenting dendritic cells when cultured in GM-CSF and IL-4, J. Leukoc. Biol., 1996, 59(2):208-18; Oehler, L. et al., Neutrophil granulocyte-committed cells can be driven to acquire dendritic cell characteristics, J. Exp. Med., 1998, 187(7):1019-28). Regarding flow cytometry, see the references by Okano et al. and Stites et al. (Okano, S. et al., Recombinant Sendai virus vectors for activated T lymphocytes. Gene Ther., 2003, 10(16):1381-91; Stites, D. et al., Flow cytometric analysis of lymphocyte phenotypes in AIDS using monoclonal antibodies and simultaneous dual immunofluorescence, Clin. Immunol. Immunopathol., 1986, 38:161-177). The expression of each of the markers may be determined, for example, using as a threshold the fluorescence intensity that makes a positive rate of 1% or less when stained with an isotype control antibody, wherein the fluorescence equal to or above the threshold is deemed positive, and the fluorescence below deemed negative.

Dendritic cells or precursor cells thereof can be prepared according to or based on known methods. For example, the cells can be isolated from blood (for example, peripheral or cord blood), bone marrow, lymph nodes, other lymphatic organs, spleen, and skin (Bishop et al., Blood 83: 610-616, 1994; Bontkes, H. J. et al. (2002) J. Leukoc. Biol. 72, 321-329; Katsuaki, S. et al. (1998) CRYOBIOLOGY 37, 362-371; Ladan, K. et al. (2006) Stem Cells 24, 2150-2157; Ueda, T. et al. (2000) J. Clin. Invest. 105: 1013-1021). Dendritic cells to be used in the context of the present invention are preferably obtained from blood or bone marrow. Alternatively, dendritic cells to be used in the present invention may be skin Langerhans cells, veiled cells of afferent lymphatics, follicular dendritic cells, spleen dendritic cells, and interdigitating cells of lymphatic organs. The dendritic cells used in the present invention include dendritic cells selected from the group consisting of CD34+-derived dendritic cells, bone marrow-derived dendritic cells, monocyte-derived dendritic cells, splenic cell-derived dendritic cells, skin-derived dendritic cells, follicular dendritic cells, and germinal center dendritic cells. In particular, preferred DC precursor cells are hematopoietic stem cells, hematopoietic progenitor cells, and the like, obtained from bone marrow, cord blood, or peripheral blood. Hematopoietic stem cells or hematopoietic progenitor cells can be isolated by negative selection using commercially available kits or such, or by positive selection using CD34+ or such (see U.S. patent application Ser. No. 08/539, 142). For example, cell isolation methods that use surface antigens by magnetic beads, fluorescent label sorting, biotin-avidin binding carriers, and such are known (Berenson et al., J. Immunol. Meth., 91:11, 1986; WO 93/08268).

When DCs or DC precursor cells are selected (or enriched) from a composition including DCs or DC precursor cells and other cells, it is preferable to perform so-called negative selection which removes cells other than the DCs or DC precursor cells. Through the negative selection process, precursors of DC-granulocytes (J. Exp. Med., 1998, 187: 1019-1028; Blood, 1996, 87: 4520-4530) remain without being removed and thus, it is considered that not only DCs differentiated from adherent CD14+ cells but also DCs differentiated from precursors can be recovered together. This is expected to reduce the cytotoxicity that occurs, for example, when vectors are introduced into DCs.

For example, by removing T cells, NK cells, B cells, and the like, using antibodies specific thereto, DCs can be enriched. Specifically, for example, it is preferable to obtain cells with low or negative expression of a surface marker selected from CD2, CD3, CD8, CD19, CD56, and CD66b, or any combinations thereof. More preferred are cells in which the expressions of CD2, CD3, CD8, CD19, CD56, and CD66b are all low or negative. Therefore, it is preferable to remove cells expressing these markers using antibodies against the markers (Hsu et al., Nature Med. 2:52 (1996)). The negative selection can be performed using polyvalent antibodies. Alternatively, a similar selection can also be performed using beads or the like for magnetic cell separation (MACS). The use of beads is preferred for large scale cell preparation, such as collection of mononuclear cells through blood cell separation or the like. For example, DC precursor cells prepared by negative selection from monocytes that were enriched from a cell solution obtained from the body can be suitably used in the context of the present invention.

Specific methods for isolating dendritic cells are described in, for example, Cameron et al., Science 257:383 (1992); Langhoff et al., Proc. Natl. Acad. Sci. USA 88:7998 (1991); Chehimi et al., J. Gen. Virol. 74:1277 (1993); Cameron et al., Clin. Exp. Immunol. 88:226 (1992); Thomas et al., J. Immunol. 150:821 (1993); and Karhumaki et al., Clin. Exp. Immunol. 91:482 (1993). The isolation of dendritic cells by flow cytometry is described in, for example, Thomas et al., J. Immunol. 153:4016 (1994); Ferbas et al., J. Immunol. 152: 4649 (1994); and O'Doherty et al., Immunology 82:487 (1994). In addition, magnetic cell separation is described in, for example, Miltenyi et al., Cytometry 11: 231-238 (1990).

Furthermore, for example, human dendritic cells may be isolated and proliferated using the methods described in Macatonia et al., Immunol. 74:399-406 (1991); O'Doherty et al., J. Exp. Med. 178:1067-1078 (1993); Markowicz et al., J. Clin. Invest. 85:955-961 (1990); Romani et al., J. Exp. Med. 180:83-93 (1994); Sallusto et al., J. Exp. Med. 179:1109-1118 (1994); Berhard et al., J. Exp. Med. 55:1099-1104 (1995); and the like. Moreover, dendritic cells can be formed from CD34+ cells obtained from bone marrow, cord blood, peripheral blood, or the like and from peripheral blood-derived mononuclear cells by the method described in Van Tendeloo et al., Gene Ther. 5:700-707 (1998).

DC precursor cells are expanded in a medium containing one or more cytokines. For example, DC precursor cells can be expanded over about ten days even with IL-3 alone. However, expansion over a longer period is not seen with IL-3 alone. The present inventors discovered that by culturing DC precursor cells in a medium containing SCF and IL-3, cells having the ability to differentiate into DCs can be efficiently expanded. Thus, for expansion for two weeks or longer, IL-3 and SCF are preferably used in combination. In particular, DC precursor cells having a strong ability to differentiate into DCs can be obtained in large quantities by culturing DC precursor cells in a medium containing the following four types of cytokines: FLT-3L, SCF, IL-3, and IL-6. The present invention relates to methods for producing DCs, which comprise the step of expanding DC precursor cells in a medium containing IL-3 and SCF but not FLT-3L and IL-6; a medium containing FLT-3L, SCF, and IL-3 but not IL-6; or a medium containing SCF, IL-3, and 1L-6 but not FLT-3L. The present invention also relates to methods for producing DCs, which comprise the step of expanding DC precursor cells in a medium containing FLT-3L, SCF, IL-3, and IL-6; for example, a medium containing these cytokines but not a significant amount of one or more cytokines (or any combination thereof) selected from G-CSF, GM-CSF, IL-4, and TNFα.

Meanwhile, in the culture described herein in the presence of a combination of cytokines, the combination may additionally include other cytokines (i.e., the culture is carried out in the presence of other additional cytokines), or may not include any other additional cytokine. Alternatively, it is possible to include or not to include the additional step of culturing in the presence of other cytokines. In the culture described herein in the presence of a combination of cytokines, it is, for example, possible to use any combination of one or more selected from the group consisting of GM-CSF, SCF, IL-4, IL-3, TPO, Flt-3L, and IL-6. The specification also discloses cases that exclude an arbitrary combination of one or more cytokines selected from the group. It is possible to include or not to include the additional step of culturing in the presence of an arbitrary combination of one or more cytokines selected from the group. The specification also discloses cases that exclude the step of culturing in the presence of an arbitrary combination of one or more cytokines selected from the group. For example, when saying "using GM-CSF and SCF", it may mean additionally including "an arbitrary combination of one or more selected from the above-described group of cytokines, but excluding GM-CSF and SCF, i.e., the group consisting of IL-4, IL-3, TPO, Flt-3L, and IL-6" or it may mean "not including an arbitrary combination of one or more selected from the group". It is possible to include or not to include the additional step of culturing in the presence of an arbitrary combination of one or more. For example, the culture may be carried out without using TPO, without using Flt-3L, without using IL-6, without using TPO and Flt-3L, without using TPO and IL-6, without using Flt-3L and IL-6, or without using Flt-3L, TPO, and IL-6. The same can be applied to other combinations of cytokines. Such combinations are all taught herein.

In the culture of the present invention, for example, GM-CSF (for example, human GM-CSF) may be used at 100 ng/ml or less, 50 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; SCF (for example, human SCF) may be used at 50 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; IL-4 (for example, human IL-4) may be used at 50 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; IL-3 (for example, human IL-3) may be used at 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; TPO (for example, human TPO) may be used at 50 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; Flt3-L (for example, human Flt3-L) may be used at 100 ng/ml or less, 50 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; IL-6 (for example, human IL-6) may be used at 25 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; G-CSF (for example, human G-CSF) may be used at 100 ng/ml or less, 50 ng/ml or less, 25 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; TNF-α (for example, human TNF-α) may be used at 100 ng/ml or less, 50 ng/ml or less, 25 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; c-kit ligand (for example, human c-kit ligand) may be used at 100 ng/ml or less, 50 ng/ml or less, 25 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used; IL-13 (for example, human IL-13) may be used at 100 ng/ml or less, 50 ng/ml or less, 25 ng/ml or less, 10 ng/ml or less, 5 ng/ml or less, 1 ng/ml or less, 0.5 ng/ml or less, 0.1 ng/ml or less, 0.05 ng/ml or less, 0.01 ng/ml or less, 0.005 ng/ml or less, 0.001 ng/ml or less, 0.0005 ng/ml or less, 0.0001 ng/ml or less, 0.00005 ng/ml or less, 0.00001 ng/ml or less, or may not be used. These may be used in any combination. Such combinations are all taught herein.

FLT-3L (Fms-like tyrosine kinase 3 ligand) is a ligand for Flt-3, and promotes the differentiation and proliferation of hematopoietic precursor cells (Namikawa R. et al., BLOOD 87: 1881-1890 (1996)). The group of polypeptides described in EP 0627487 A2 and WO 94/2839 are included in the Flt-3L of the present invention. Human FLT-3L cDNA is available under the accession number ATCC 69382 from American Type Culture Collection (ATCC). SCF is also referred to as c-kit ligand, mast cell growth factor (MGF), or steel factor (Zsebo et al., Cell 63: 195-201 (1990); Huan, E. Cell 63: 225-233; Williams, D. E., Cell 63: 167-174 (1990); Toksoz. D et al, PNAS 89: 7350-7354 (1992)). SCF includes the polypeptides described in EP 423,980.

IL (interleukin)-3 is a hematopoietic factor produced by activated T cells, mast cells, and eosinophils. IL-3 of the present invention includes the IL-3 polypeptides described in U.S. Pat. No. 5,108,910. A DNA sequence encoding the human IL-3 protein is available under the accession number ATCC 67747. IL-6 was discovered as a B cell differentiation-inducing factor. IL-6 has pleiotropic physiological activities in addition to those involved in the antibody production system, such as induction of biosynthesis of acute-phase proteins in the liver and promotion of hematopoietic stem cell proliferation based on the synergistic effect with IL-3 (Paul S R et al., Blood, 1991, 77: 1723-1733). IL-4 is produced mainly by helper T cells, and has broad physiological activities on T cells, B cells, and other blood cells (Mosley et al., Cell 59: 335 (1989); Idzerda et al., J. Exp. Med. 171: 861 (1990); Galizzi et al., Intl. Immunol. 2: 669 (1990)). GM-CSF is a cytokine that was isolated as a factor that stimulates the growth of colonies containing macrophages or granulocytes (U.S. Pat. Nos. 5,108,910 and 5,229,496).

GM-CSF is an essential factor for growth and development of precursor cells of granulocytes and macrophages, and stimulates myeloblasts and monoblasts to induce their differentiation.

Thrombopoietin (TPO) is a hematopoietic cytokine, which has a function to enhance the production of megakaryocytes by specifically acting on the process of production of megakaryocytes from hematopoietic stem cells (Japanese Patent No. 3058353).

The concentration of each cytokine may be appropriately adjusted; however, the concentration of FLT-3L may be, for example, 5 ng/ml or more, 10 ng/ml or more, 20 ng/ml or more, or 30 ng/ml or more, 800 ng/ml or less, 600 ng/ml or less, 500 ng/ml or less, 300 ng/ml or less, 200 ng/ml or less, or 100 ng/ml or less, for example, about 5 to 35 ng/ml, preferably about 10 to 30 ng/ml, more preferably about 15 to 25 ng/ml, and still more preferably about 20 ng/ml. The concentration of GM-CSF may be, for example, 0.5 ng/ml or more, 1 ng/ml or more, 5 ng/ml or more, 10 ng/ml or more, 20 ng/ml or more, or 30 ng/ml or more, 800 ng/ml or less, 600 ng/ml or less, 500 ng/ml or less, 300 ng/ml or less, 200 ng/ml or less, or 100 ng/ml or less. The concentration of SCF may be, for example, 0.25 ng/ml or more, 0.5 ng/ml or more, 1 ng/ml or more, 5 ng/ml or more, 10 ng/ml or more, 20 ng/ml or more, or 30 ng/ml or more, 800 ng/ml or less, 600 ng/ml or less, 500 ng/ml or less, 300 ng/ml or less, 200 ng/ml or less, 100 ng/ml or less, or 50 ng/ml or less. The concentration of IL-4 may be, for example, 0.5 ng/ml or more, 1 ng/ml or more, 5 ng/ml or more, 10 ng/ml or more, 20 ng/ml or more, or 30 ng/ml or more, 800 ng/ml or less, 600 ng/ml or less, 500 ng/ml or less, 300 ng/ml or less, 200 ng/ml or less, 100 ng/ml or less, or 50 ng/ml or less. The concentrations of IL-6, TPO, and other cytokines may be, for example, 1 ng/ml or more, 2 ng/ml or more, 5 ng/ml or more, 10 ng/ml or more, 20 ng/ml or more, or 30 ng/ml or more, 800 ng/ml or less, 600 ng/ml or less, 500 ng/ml or less, 300 ng/ml or less, 200 ng/ml or less, 100 ng/ml or less, 50 ng/ml or less, 25 ng/ml or less, or 10 ng/ml or less.

When using a GM-CSF-free medium such as FS36, the concentrations of SCF, IL-3, and IL-6 are about 3 to 20 ng/ml, preferably about 5 to 15 ng/ml, more preferably about 7 to 12 ng/ml, and still more preferably about 10 ng/ml, but are not limited thereto. These may be used in any combination. Such combinations are all taught herein. For example, RPMI1640 or IMDM can be used as a culture medium. The medium is appropriately supplemented with 5% to 20% serum, preferably about 10% serum, and preferably fetal bovine serum (FBS). Culture of DC precursor cells can be started at about $1 \times 10^5$ to $5 \times 10^5$ cells/ml, for example, at about $2.5 \times 10^5$ cells/ml. Preferably, the cells are passaged every three or four days. When passaging, the cell concentration is preferably adjusted to $2 \times 10^6$ cells/ml or a lower concentration. When primate DC precursor cells such as human $CD34^+$ cells or human $CD14^+$ cells are cultured using GM-CSF and SCF in combination, GM-CSF may be used, for example, at about 1 to 500 ng/ml (about 1 to 200 ng/ml or about 1 to 100 ng/ml), more preferably about 2 to 300 ng/ml, for example, about 5 to 200 ng/ml, preferably about 10 to 150 ng/ml, more preferably about 20 to 120 ng/ml, and still more preferably about 30 to 100 ng/ml. Meanwhile, SCF may be used, for example, about 0.5 to 500 ng/ml (about 0.5 to 100 ng/ml or about 0.5 to 50 ng/ml), more preferably about 1 to 300 ng/ml, even more preferably about 2 to 200 ng/ml, and still more preferably about 5 to 100 ng/ml, for example about 10 to 70 ng/ml, more preferably, for example, about 20 to 60 ng/ml, and still more preferably about 25 to 50 ng/ml.

When primate DC precursor cells such as human $CD34^+$ cells are cultured using IL-3 and SCF in combination, IL-3 may be used, for example, at about 0.1 to 10 ng/ml, preferably about 1 to 10 ng/ml, and more preferably about 10 ng/ml. SCF may be used, for example, at about 0.5 to 500 ng/ml (about 0.5 to 100 ng/ml or about 0.5 to 50 ng/ml), more preferably about 1 to 300 ng/ml, even more preferably about 2 to 200 ng/ml, and still more preferably about 5 to 100 ng/ml, for example, about 10 to 70 ng/ml, more preferably, for example, about 20 to 60 ng/ml, more preferably about 25 to 50 ng/ml.

When primate DC precursor cells such as human $CD34^+$ cells are cultured using TPO and SCF in combination, TPO may be used, for example, at about 0.5 to 50 ng/ml, preferably about 5 to 50 ng/ml, and more preferably about 50 ng/ml. SCF may be used, for example, at about 0.5 to 500 ng/ml (about 0.5 to 100 ng/ml or about 0.5 to 50 ng/ml), more preferably about 1 to 300 ng/ml, even more preferably about 2 to 200 ng/ml, and still more preferably about 5 to 100 ng/ml, for example, about 10 to 70 ng/ml, more preferably, for example, about 20 to 60 ng/ml, more preferably about 25 to 50 ng/ml.

When primate DC precursor cells such as human $CD34^+$ cells are cultured using Flt-3L and SOF in combination, Flt-3L may be used, for example, at about 1 to 100 ng/ml, preferably about 10 to 100 ng/ml, and more preferably about 100 ng/ml. SCF may be used, for example, at about 0.5 to 500 ng/ml (about 0.5 to 100 ng/ml or about 0.5 to 50 ng/ml), more preferably about 1 to 300 ng/ml, even more preferably about 2 to 200 ng/ml, and still more preferably about 5 to 100 ng/ml, for example, about 10 to 70 ng/ml, more preferably, for example, about 20 to 60 ng/ml, more preferably about 25 to 50 ng/ml.

When primate DC precursor cells such as human $C34^+$ cells are cultured using Flt-3L, SCF, TPO, and IL-6 in combination, Flt-3L may be used, for example, at about 1 to 100 ng/ml, preferably about 10 to 100 ng/ml, and more preferably about 100 ng/ml. SCF may be used, for example, at about 0.5 to 500 ng/ml (about 0.5 to 100 ng/ml or about 0.5 to 50 ng/ml), more preferably about 1 to 300 ng/ml, even more preferably about 2 to 200 ng/ml, and still more preferably about 5 to 100 ng/ml, for example, about 10 to 70 ng/ml, more preferably, for example, about 20 to 60 ng/ml, more preferably about 25 to 50 ng/ml. TPO may be used, for example, at about 0.5 to 50 ng/ml, preferably about 5 to 50 ng/ml, and more preferably about 50 ng/ml. IL-6 may be used, for example, at about 0.25 to 25 ng/ml, preferably about 2.5 to 25 ng/ml, and more preferably about 25 ng/ml.

When primate DC precursor cells such as human $CD34^+$ cells are cultured using GM-CSF and IL-4 in combination, GM-CSF may be used, for example, at about 1 to 500 ng/ml (about 1 to 200 ng/ml or 1 to 100 ng/ml), more preferably about 2 to 300 ng/ml, for example, about 5 to 200 ng/ml, preferably about 10 to 150 ng/ml, more preferably about 20 to 120 ng/ml, and still more preferably about 30 to 100 ng/ml. IL-4 may be used, for example, at about 0.5 to 50 ng/ml, preferably about 5 to 50 ng/ml, and more preferably about 50 ng/ml.

The present inventors found that, by adjusting the period of DC precursor cell expansion to about three to four weeks, the efficiency of subsequent differentiation into DCs can be markedly increased. Longer culture period yields more cells but reduces the efficiency of differentiation into DCs. In particular, the efficiency of differentiation into DCs is markedly reduced with DC precursor cells expanded for five weeks in FS36 medium. Accordingly, if a GM-CSF-free medium, for example, FS36 is used, the period of DC precursor cell culture is about three to about four weeks, preferably about three weeks, for example, 18 to 24 days, and more preferably 20 to 22 days; and it is preferable to avoid expansion of DC precursor cells for a longer period in a medium containing the same combination of cytokines. After culturing for these periods, DCs are cultured and differentiated in a DC differentiation medium as described below. For example, when DC precursor cells are cultured in a medium containing FLT-3L, SCF, IL-3, and IL-6, after culturing for the period indicated above, they are cultured in a medium other than one that contains all of FLT-3L, SCF, IL-3, and IL-6.

Furthermore, the present invention includes the step of culturing cells expanded in media containing one or more cytokines in the presence of GM-CSF and IL-4. Culture period in the presence of GM-CSF and IL-4 is about three to 14 days, preferably seven days (for example, five days or more, preferably six days or more, nine days or less, preferably eight days or less).

In a preferred embodiment, the methods of the present invention enable production of dendritic cells with a high IL-12 productivity. The IL-12 productivity can be determined, for example, as follows. For example, human cord blood-derived $CD34^+$ cells are cultured via the first step of the methods, specifically, cultured for four weeks in the presence of stem cell factor (SCF) and a cytokine selected from the group consisting of (i) to (v) below. IMDM supplemented with 10% FBS can be used as a medium.

(i) GM-CSF, (ii) IL-3, (iii) TPO, (iv) Flt-3L, (v) Flt-3L, TPO, and IL-6

Then, the cells are cultured via the second step, specifically, cultured for one week in the presence of GM-CSF and IL-4. Next, the cells are treated with OK432, specifically, cultured for two days (48 h) in IMDM supplemented with 10% FBS containing OK432 (0.5 KE/ml) (Chugai Pharmaceutical Co.; Japan Standard Commodity Classification No. 874299). Then, the IL-12 released into the culture medium during the two days is quantified by ELISA or the like.

Figure 3:
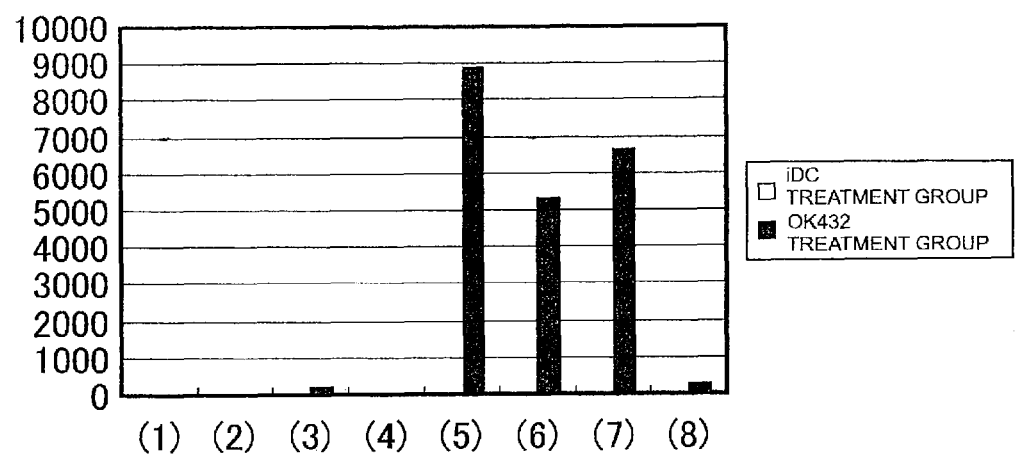
FIG. 3(A) depicts graphs showing the result of quantitation of cytokine (IL-12) produced by human cord blood-derived CD34$^+$ cells cultured for 35 days in a medium containing particular cytokine(s). The unit of the vertical axis is "pg/ml/48h" ($1 \times 10^6$ cells were cultured in 1 ml of medium). Dishes with a diameter of 3.5 cm were used to culture the cells. The amount of produced IL-12 was determined by ELISA. The cells were cultured for 35 days in a medium containing the particular cytokine(s) indicated in this figure. This figure shows the amounts of IL-12 production by cells in a sample treated with iDC after 35 days of culture (indicated as "iDC treatment group" in this figure) and cells in a sample treated with iDC after 35 days of culture in a medium containing particular cytokines (iDC treatment followed by OK432 treatment) (indicated as "OK432 treatment group" in this figure). The amount of IL-12 production in the sample after "OK432 treatment" to activate dendritic cells ("OK432 treatment group") was determined relative to the "iDC treatment group". The result is shown in the figure. The samples of (1) to (8) shown in this figure are described below in detail. Values shown in the parentheses correspond to those of the vertical axis for each sample (rounded to two decimal places). (1) A sample obtained after culturing CD34$^+$ cells for five weeks under GMSCF administration group culture conditions (0.02 in the iDC treatment group; 5.96 in the OK432 administration group). (2) A sample obtained after culturing CD34$^+$ cells for four weeks under IL-3 administration group culture conditions, followed by one week of culture under GMIL-4 administration group culture conditions (0 in the iDC treatment group; 21.12 in the OK432 administration group). (3) A sample obtained after culturing CD34$^+$ cells for four weeks under GMSCF administration group culture conditions, followed by one week of culture under GMIL-4 administration group culture conditions (0.42 in the iDC treatment group; 210.55 in the OK432 administration group). (4) A sample obtained after culturing CD34$^+$ cells for four weeks under IL-3SCF administration group culture conditions, followed by one week of culture under GMIL-4 administration group culture conditions (0 in the iDC treatment group; 71.40 in the OK432 administration group). (5) A sample obtained after culturing CD34$^+$ cells for four weeks under TPOSCF administration group culture conditions, followed by one week of culture under GMIL-4 administration group culture conditions (0 in the iDC treatment group; 8891.03 in the OK432 administration group). (6) A sample obtained after culturing CD34+ cells for four weeks under FS administration group culture conditions, followed by one week of culture under GMIL-4 administration group culture conditions (0.22 in the iDC treatment group; 5333.57 in the OK432 administration group). (7) A sample obtained after culturing CD34+ cells for four weeks under FST6 administration group culture conditions, followed by one week of culture under GMIL-4 administration group culture conditions (0 in the iDC treatment group; 6631.32 in the OK432 administration group). (8) A sample obtained after culturing CD14+ cells for one week under GMIL4 administration group culture conditions (0.55 in the iDC treatment group; 283.76 in the OK432 administration group). This culture sample is known to be dendritic cells that produce IL-12 (JP-A (Kohyo) 2008-515439), and was used as a control in the experiment.
FIG. 3(B) shows more details of the data of some samples indicated in FIG. 3(A). As is the case in FIG. 3(A), the vertical axis indicates the amount of IL-12 production, and the unit of the vertical axis is "pg/1e6 cell/ml/48h". The amount of IL-12 production was determined by ELISA. The details of the samples of (1) to (4) and (8) in this figure are same as those of FIG. 3(A).
Figure 3:
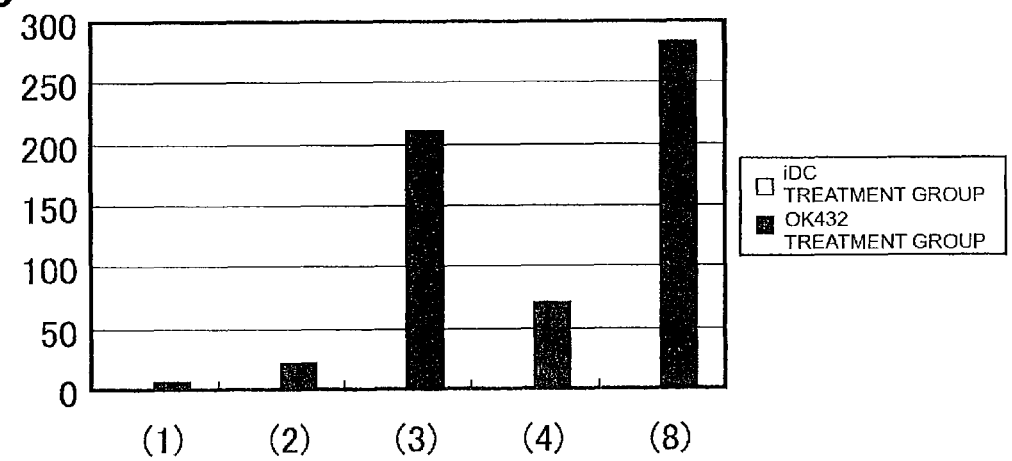

Via the above-described OK432 treatment, the methods of the present invention enable production of IL-12 in an amount of, for example, 50 or more, preferably 60 or more, 70 or more, 80 or more, 90 or more, 100 or more, 150 or more, 200 or more, 250 or more, 300 or more, 400 or more, 500 or more, 1000 or more, 2000 or more, 3000 or more, 4000 or more, 5000 or more, 6000 or more, 7000 or more, or 8000 or more (the unit is described in the legend of FIG. 3). (i) When GM-CSF is used in the above-described first step in particular, the methods may enable production of IL-12 in an amount of, for example, 50 or more, 100 or more, preferably 200 or more. (ii) When IL-3 is used in the above-described first step, the methods may enable production of IL-12 in an amount of, for example, 20 or more, 30 or more, 40 or more, preferably 50 or more. (iii) When TPO is used in the above-described first step, the methods may enable production of IL-12 in an amount of, for example, 100 or more, 200 or more, 500 or more, 1000 or more, 3000 or more, 4000 or more, preferably 5000 or more. (iv) When Flt-3L is used in the above-described first step, the methods may enable production of IL-12 in an amount of, for example, 100 or more, 200 or more, 500 or more, 1000 or more, 3000 or more, 4000 or more, preferably 5000 or more. (v) When Flt-3L, TPO, and IL-6 are used in the above-described first step, the methods may enable production of IL-12 in an amount of for example, 100 or more, 200 or more, 500 or more, 1000 or more, 3000 or more, 4000 or more, preferably 5000 or more.

Primate $CD34^+$ cells include, for example, cord blood-derived $CD34^+$ cells, bone marrow-derived $CD34^+$ cells, and peripheral blood-derived $CD34^+$ cells.

It is possible to use an appropriate desired medium as culture solution. Such culture solutions include, for example, DMEM (Dulbecco's Modified Eagle Medium), MEM (Minimum Essential Medium), RPMI-1640, X-VIVO™ (Lonza), and IMDM (Iscove's Modified Dulbecco's Medium). IMDM is used most preferably. Preferably, the media are appropriately supplemented with serum, for example, at 1% to 20% (v/v), more preferably 2% to 20%, even more preferably 5% to 15%, and still more preferably 5% to 10% (for example, about 10%). The serum is preferably bovine-derived serum, and most preferably fetal calf serum (FCS). Culturing temperature is not limited and can be, for example, 32° C. to 39° C., 35° C. to 38° C., or about 37° C. $CO_2$ is also not limited and can be, for example, about 5% (4% to 6%).

The present invention provides compositions for expanding dendritic cells, compositions for preparing dendritic cells, compositions for producing dendritic cells, media for expanding dendritic cells, media for preparing dendritic cells, and media for producing dendritic cells, all of which comprise SCF and a cytokine(s) of any one of groups (i) to (v) below:
(i) granulocyte/macrophage-colony stimulating factor (GM-CSF)
(ii) IL-3
(iii) TPO
(iv) Flt-3L
(v) Flt-3L, TPO, and IL-6

In the present invention, the compositions for expanding dendritic cells, compositions for preparing dendritic cells, compositions for producing dendritic cells, media for expanding dendritic cells, media for preparing dendritic cells, and media for producing dendritic cells may comprise GM-CSF and IL-4 in addition to SCF and a cytokine(s) of any one of groups (i) to (v) described above.

Furthermore, the compositions may appropriately comprise sterilized water, buffers, salts, and the like. The culture media include the culture solutions described above, but are not limited thereto. The media may or may not contain sera. Further, the media may or may not contain antibiotics.

The present invention also relates to uses of SCF and a cytokine of any one of groups (i) to (v) below in producing a composition or medium described above:
(i) granulocyte/macrophage-colony stimulating factor (GM-CSF)
(ii) IL-3
(iii) TPO
(iv) Flt-3L
(v) Flt-3L, TPO, and IL-6

The present invention also relates to uses of SCF and the cytokine of any one of groups (i) to (v) above, and GM-CSF and IL-4, in producing a composition or medium described above.

The present invention also relates to kits for expanding dendritic cells, kits for preparing dendritic cells, and kits for producing dendritic cells, all of which comprise (i) to (v) mentioned above and SCF as components. The kits may further comprise culture solutions (for example, not containing serum) or powder for preparing culture solutions (containing amino acids, salts, and the like, but not containing any serum, antibiotic, and such). Preferably, these compositions, media, and kits are intended for expanding, preparing, and producing primate dendritic cells including human dendritic cells, and more preferably, for expanding, preparing, and producing dendritic cells with a high IL-12 productivity from primate $CD34^+$ cells including human $CD34^+$ cells. Preferably, they do not contain TNF-α and/or IL-4. For example, the concentrations of TNF-α and IL-4 in the composition and medium are preferably in a range that does not significantly exceed their concentrations in the serum when serum is added. For example, the concentrations are preferably three times, two times, one time or lower than the cytokine concentrations in the serum (for example, normal FCS), and are preferably one half or lower, more preferably one third or lower, or one fifth or lower, specifically 50 ng/ml or lower, preferably 40, 30, 20, 10, 5, 3, or 1 ng/ml, or lower. When serum is not added, preferably only GM-CSF and SCF are included as cytokines.

According to the methods of the present invention, DCs can be expanded from $CD34^+$ cells by, for example, $10^2$ times, preferably $0.5 \times 10^3$ times, more preferably $1 \times 10^3$ times, even more preferably $0.5 \times 10^4$ times, still more preferably $1 \times 10^4$ times, yet more preferably $0.5 \times 10^5$ times, even still more preferably $1 \times 10^5$ times, and still yet more preferably $0.5 \times 10^6$ times or more. For example, with one week-culture, the cells can be increased at a rate of 5 times, preferably 6, 7, 8, 9, 10, 11, 12, or 13 times or higher. The expanded cells contain a high purity of DCs (iDCs). The percentage of CD11c-positive cells in the expanded cells (the ratio of $CD11c^+$ cells in the total cells) is, for example, 30% or higher, preferably 40% or higher, more preferably 50% or higher, 60% or higher, 70% or higher, 75% or higher, 80% or higher, or 85% or higher. Furthermore, mature DCs can be obtained by treating iDCs with LPS, Poly(I:C), Sendai virus, OK432, or such.

The dendritic cells with a high IL-12 productivity obtained by the methods of the present invention are useful as DC vaccines which are useful in immunotherapy for infections, cancers, and other diseases of interest for which beneficial effects can be expected from immune induction. For example, in tumor immunotherapy, dendritic cells are made to present tumor antigens by mixing dendritic cells with tumor cell lysates, pulsing with peptides, introducing tumor antigen genes into dendritic cells, or such. The resulting dendritic cells can be used in DC therapy against tumors.

For example, the method of introducing tumor antigen genes into dendritic cells can be expected to prolong the duration of tumor antigen presentation in vivo as compared with tumor lysates and peptide pulses, and also has the advantage of not being limited by HLA (in the case of peptides: a certain peptide derived from an antigen is used; however, due to the requirement of HLA binding, when the HLA type changes, the peptide region used in the antigen also changes).

For example, DC precursor cells expanded by the methods of the present invention are differentiated into DCs by culturing the precursor cells in the presence of CM-CSF and SCF and further by culturing the cells in the presence of GM-CSF and IL-4, and then the DCs are activated by culturing in the presence of OK432, RNA viruses, or the like. The culture period may be appropriately adjusted and is, for example, two to seven days. For example, when used for immunostimulation (e.g., tumor immunity), RNA viruses such as minus-strand RNA viruses can be used for gene transfer, and the RNA virus infection itself induces the activation of dendritic cells. Thus, it is possible to omit the step of activation by cytokine treatment and the like after introduction, which is expected to contribute to maintenance of cell viability, reduction in cost, and further reduction in the time required for ex vivo manipulation. Activated T cells, in particular, tumor specific cytotoxic T cells and the like, which are required for T cell transfer therapy can be efficiently and easily induced ex vivo in a short period by using dendritic cells into which genes have been introduced using RNA viral vectors (WO 2005/042737; WO 2006/001122).

DCs can be appropriately formulated into compositions in combination with pharmaceutically acceptable carriers. Examples of carriers include desired solutions that can be used to suspend viable cells, such as physiological saline, phosphate buffered saline (PBS), culture solutions, and serum. The compositions may comprise antigenic peptides to be presented on dendritic cells. Furthermore, when DCs are used as vaccines, immunostimulants such as cytokines, cholera toxin, and Salmonella toxin may be added to the vaccine compositions to increase immunogenicity. Moreover, the vaccine may be combined with adjuvants, such as alum, incomplete Freund's adjuvant, MF59 (oil emulsion), MTP-PE (muramyl tripeptide derived from cell wall of mycobacteria), and QS-21 (derived from soapbark tree *Quilaja saponaria*).

Antigens can be presented on DCs by mixing DCs with a cell lysate antigen by pulsing peptides, or by introducing an antigen gene-encoding vector into DCs. Antigens include desired antigens related to infectious microorganisms, viruses, parasites, pathogens, cancers, and the like. These may be structural or non-structural proteins. Such antigens (or processed peptides thereof) bind to MHC molecules on the surface of dendritic cells, and are presented on the cell surface, inducing immune responses.

When used as a vaccine, the antigens can be applied to, for example, tumors, infectious diseases, and other general diseases. To treat infectious diseases, for example, epitopes of an antigen protein of an infectious microorganism may be analyzed, and then expressed or presented by dendritic cells.

Antigens derived from pathogens include, for example, proteins of hepatitis A virus, hepatitis B virus, hepatitis C virus, hepatitis delta virus, papilloma virus antigen, herpes simplex virus (HSV), varicella-zoster virus (VZV), Epstein-Barr virus, Cytomegalovirus (CMV), HIV, malaria, and the like, or partial peptides thereof (G. L. Mandell et al. (Ed.) Hinman et al., Principles and Practice of Infectious Diseases, 3rd Ed., Churchill Livingstone Inc., NY, pp. 2320-2333). DCs presenting these antigens can be used prophylactically or therapeutically against the infectious diseases. Specifically, envelopes of influenza highly-virulent strain H5N1 for influenza, envelope proteins of Japanese encephalitis virus (Vaccine, vol. 17, No. 15-16, 1869-1882 (1999)) for Japanese encephalitis, HIV and SIV gag proteins (J. Immunology (2000) vol. 164, 4968-4978), HIV envelope proteins, Nef protein, and other viral proteins for AIDS can be mentioned. In addition, for example, cholera toxin B subunit (CTB) (Arakawa T, et al., Nature Biotechnology (1998) 16(10): 934-8, Arakawa T, et al., Nature Biotechnology (1998) 16(3): 292-7) for cholera; rabies virus glycoprotein (Lodmell D L et al., 1998, Nature Medicine 4(8):949-52) for rabies; and capsid protein L1 of human papilloma virus type 6 (J. Med. Virol, 60, 200-204 (2000)) for cervical carcinoma can be mentioned. Furthermore, it is possible to use JE-E antigen protein of Japanese encephalitis (Japanese Patent Application Kokai Publication No. (JP-A) S64-74982 (unexamined, published Japanese patent application), JP-A (Kokai) H01-285498), gD2 protein of human herpes simplex virus (JP-A (Kokai) H05-252965), polypeptides derived from hepatitis C virus (JP-A (Kokai) H05-192160), polypeptides derived from pseudorabies virus (JP-A (Kohyo) H07-502173), and the like. For example, cells derived from patients infected with such pathogenic microorganisms may be analyzed to identify an epitope of an antigen protein presented on antigen-presenting cells (APC) for use. It is also preferable to appropriately select the HLA type and identify an epitope corresponding to the desired HLA type for use.

To specifically promote an immune response against a tumor, one or more tumor antigens are presented on the dendritic cells. Tumor-related antigens can be obtained, for example, by preparing crude tumor cell extracts or by partial purification of antigens ((Cohen et al., Cancer Res. 54: 1055 (1994); Cohen et al., Eur. J. Immunol. 24: 315 (1994); Itoh et al., J. Immunol. 153: 1202 (1994)). The obtained tumor antigens may be further purified, or may be synthesized or expressed as a recombinant peptide.

When purified dendritic cells are pulsed with (exposed to) antigens and made to take in the antigens, the antigens are processed by the DCs and presented on the cell surface (Germain, R. N., Cell 76: 287 (1994)). There are various known methods for pulsing dendritic cells with antigens, and those skilled in the art routinely select appropriate methods according to the antigen to be presented. The present invention provides compositions comprising DCs that are produced by the methods of the present invention and which present antigens, and uses thereof in immunotherapy. To stimulate immune responses, the compositions of the present invention can be administered by injection, continuous infusion, sustained release from implants, or other appropriate techniques. Typically, the compositions comprising dendritic cells are administered together with physiologically acceptable carriers, excipients, or diluents. The ones that do not show any significant toxicity to the administered individual at the dose or concentration used can be used as a carrier and include, for example, physiological saline.

The tumor antigens may be tumor cell-specific antigens (i.e., present in tumor cells but absent in non-tumor cells) or antigens that are expressed at a higher level in tumor cells than in non-tumor cells of the same type. The immune system is stimulated through the administration of the dendritic cells. When CTL acts as a major effector, a desired intercellular or extracellular tumor antigen can be used. When an antibody is reacted as the effector by using dendritic cells to activate CD4 T cells which triggers the induction of antibody production through B cell activation, it is preferred to use an antigen presented on the cell surface. For example, a cell surface receptor or cell adhesion protein can be used as the antigen. The tumor antigens include, for example, Muc-1 or Muc-1-like mucin tandem repeat peptide that induce ovarian cancer or the like (U.S. Pat. No. 5,744,144); E6 and E7 proteins of human papilloma virus, which cause cervical cancer; melanoma antigens MART-1, MAGE-1, -2, -3, gp100, and tyrosinase; prostate cancer antigen PSA; as well as CEA (Kim, C. et al., Cancer Immunol. Immunother. 47 (1998) 90-96) and Her2neu (HER2p63-71, p780-788; Eur. J. Immunol. 2000; 30: 3338-3346).

Dendritic cells that are prepared according to the present invention are useful in effective immunotherapy for cancers and infectious diseases. Immunological sensitization by dendritic cells introduced with a gene of a tumor antigen or infectious disease-related antigen or T cells stimulated with such dendritic cells serves as an effective method for inducing anti-tumor or anti-infectious disease immunity in patients. The present invention also relates to the use of dendritic cells obtained by the present method in the induction of immune response. Specifically, the present invention relates to the use of dendritic cells obtained by the present method in immunotherapy, in particular, for example, in the treatment of tumors or infectious diseases. Furthermore, the present invention relates to the use of dendritic cells obtained by the present method in the production of immunoactivating agents. Specifically, the present invention relates to the use of dendritic cells obtained by the present method in the production of immunotherapeutic agents, in particular, for example, antitumor agents (tumor growth suppressants) or therapeutic agents for infectious diseases.

The cells can also be applied to general diseases. To treat diabetes, for example, a peptide of an insulin fragment can be used as an epitope in type I diabetes patients or animal models thereof (Coon, B. et al., J. Clin. Invest., 1999, 104(2):189-94).

The DC compositions may further comprise soluble cytokine receptors, cytokines, or other immunoregulatory molecules (Schrader, J. W. Mol. Immunol. 28: 295 (1991)). These cytokines can be prepared as separate compositions from the DC compositions, and administered simultaneously, separately, or sequentially with DCs. In addition, by expressing a cytokine in dendritic cells, the cells stimulate the immune system, thereby enhancing immune responses against cancers or infectious microorganisms. Thus, dendritic cells introduced with a gene encoding a cytokine are also useful in the treatment of cancers and other diseases for which cytokine therapy is expected to be effective. A dendritic cell introduced with a vector carrying a gene encoding an immunostimulatory cytokine serves as an effective immune inducing agent. For example, immunostimulatory cytokines include interleukins (for example, IL-1α, IL-1β, IL-2, IL-3, IL-4, IL-6, IL-7, IL-8, IL-9, IL-10, IL-12, IL-15, IL-18, IL-19, IL-20, IL-21, IL-23, and IL-27), interferons (for example, IFN-α, IFN-β, and IFN-γ), tumor necrosis factor (TNF), transforming growth factor (TGF)-β, granulocyte colony stimulating factor (G-CSF), macrophage colony stimulating factor (M-CSF), GM-CSF, fusion proteins containing IL-3 and GM-CSF, insulin-like growth factor (IGF)-I, IGF-2, Flt-3 ligand, Fas ligand, c-kit ligand, CD40 ligand (CD40L), and other immunomodulatory proteins (such as chemokines and costimulatory molecules). These can be used alone or in combination.

The amino acid sequences of these cytokines are well known to those skilled in the art. One may refer to: for IL-4, for example, Arai et al. (1989), J. Immunol. 142(1) 274-282; for IL-6, for example, Yasukawa et al. (1987), EMBO J., 6(10): 2939-2945; for IL-12, for example, Wolf et al. (1991), J. Immunol. 146(9): 3074-3081; for IFN-α, for example, Gren et al. (1984) J. Interferon Res. 4(4): 609-617, and Weismann et al. (1982) Princess Takamatsu Symp. 12: 1-22; for TNF, for example, Pennica et al. (1984) Nature 312: 724-729; for G-CSF, for example, Hirano et al. (1986) Nature 324:73-76; and for GM-CSF, for example, Cantrell et al. (1985) Proc. Natl. Acad. Sci. (USA) 82(18): 6250-6254. More specifically, the nucleic acid sequence encoding GM-CSF includes sequences containing the sequences from position 84 to 461 of Accession number NM_000758 (corresponding to position 18 to 144 of the amino acid sequence of NP_000749). The nucleic acid sequence encoding IL-4 includes sequences containing the sequences from position 443 to 829 of Accession number NM_000589 (corresponding to position 25 to 153 of the amino acid sequence of NP_000580). Vectors can be introduced into dendritic cells by designing them to include natural genes encoding these cytokines or mutant genes that still encode functional cytokines due to the degeneracy of genetic code.

Moreover, the genes may be modified to express modified forms of the cytokines. For example, a cytokine that has two forms, precursor and matured forms (for example, those producing active fragments by cleavage of their signal peptides, or by restrictive proteolysis), may be genetically modified to express either the precursor or the matured form. Other modified fauns (for example, fusion proteins of an active fragment of a cytokine and a heterologous sequence (for example, heterologous signal peptide)) can also be used.

Dendritic cells are useful for stimulating the patient's own T cells in vivo, and are also useful for stimulating T cells in vitro. The patient's immune system can be stimulated by ex vivo immunotherapy, in which sensitized T cells are administered to the patient. For example, T cells stimulated with dendritic cells can be prepared by contacting T cells with mature dendritic cells presenting an antigen. The antigen to be presented by the dendritic cells may be a protein (or a processed product thereof) expressed from the vector or may be exogenously pulsed into the dendritic cells. The activated T cells induce CTLs.

The present invention also relates to methods for stimulating the immune system using dendritic cells produced by the methods of the present invention. For example, patients affected with infection, cancer, or the like can be treated to stimulate their immune system. These methods comprise the step of administering dendritic cells or T cells. Specifically, the methods comprise the step of administering into a patient a therapeutically effective amount of DCs produced according to the present invention, or T cells stimulated with the DCs. Immunity against a desired antigen can be induced by pulsing dendritic cells with a desired antigen peptide to make them present the antigen. When T cells are contacted with dendritic cells in vitro, it is preferable to collect T cells from the patient and carry out ex vivo administration.

The administration dose of a composition comprising DCs or T cells to a subject varies depending on the disease, patient's weight, age, sex, and symptom, purpose of administration, form of the administered composition, administration method, and the like; however, the dose can be appropriately determined by those skilled in the art. The administration route can be appropriately selected; for example, administration to the affected sites is preferable. In general, the composition can be infused by intramuscular, intraperitoneal, subcutaneous, or intravenous injection, or by direct infusion into lymph nodes. Preferably, the composition is administered to patients by subcutaneous or intraperitoneal injection, or direct infusion into lymph nodes. Patients can be administered typically with $10^5$ to $10^9$ dendritic cells, preferably $10^6$ to $10^8$ cells, and more preferably about $10^7$ cells. The number of administration can be one time, or may be multiple times within the range of clinically acceptable side effects. The subject of administration is not particularly limited, and includes, for example, birds and mammals (humans and nonhuman mammals), including chickens, quails, mice, rats, dogs, pigs, cats, bovines, rabbits, sheep, goats, monkeys, and humans, and other vertebrates.

Dendritic cells are useful as an antitumor agent. For example, tumor growth can be suppressed by administering, into tumor sites, dendritic cells presenting the tumor antigen. The tumor site refers to tumor and its surrounding area (for example, an area within 5 mm from the tumor, preferably within 3 mm from the tumor). A stronger effect can be obtained by contacting a tumor antigen with the dendritic cells prior to administration of the dendritic cells into tumors. The contact of a tumor antigen with the dendritic cells can be carried out by using a method wherein a tumor cell lysate is mixed with the dendritic cells, a method wherein the dendritic cells are pulsed with a tumor antigen peptide, or a method wherein a tumor antigen gene is introduced into and expressed by the dendritic cells.

When T cells activated with the dendritic cells are administered, for example, the T cells can be administered at a dose of about $10^5$ to $10^9$ cells, preferably $10^6$ to $10^9$ cells, and more preferably $10^8$ to $10^9$ cells per 1 $m^2$ body surface area by intravenous injection (see Ridell et al., 1992, Science 257: 238-241). The injection can be repeated at desired intervals (for example, monthly). After the administration, recipients may be monitored for any side effects during or after T cell injection, if required. In this case, it is preferred that T cells are obtained from the same patient from whom the dendritic cells have been derived. Alternatively, the T cells may be collected from a patient, while the dendritic cells to stimulate the T cells may be derived from an HLA-compatible healthy donor. Conversely, the dendritic cells may be collected from a patient, while the T cells may be derived from an HLA-compatible healthy donor.

Cells containing the dendritic cells as the active ingredient of vaccines that are produced according to the present invention are inoculated as therapeutic vaccines to the human body. Thus, the growth capacity can be made deficient to increase safety. For example, it is known that the growth capacity of cord blood-derived monocytes is extremely reduced after the induction of differentiation. However, to use the cells as safer cell vaccines, the growth capacity can be eliminated without losing the vaccine function by treating the cells with heat, radiation, mitomycin C (MMC), or the like. For example, when X-ray irradiation is used, X-ray can be irradiated at a total radiation dose of 1000 to 3300 Rad. With regard to the mitomycin C treatment, mitomycin C can be added to the dendritic cells at a concentration of 25 to 50 µg/ml and incubated at 37° C. for 30 to 60 minutes. When the cells are treated with heat, for example, the cells can be subjected to a heat treatment of 50° C. to 65° C. for 20 minutes.

EXAMPLES

Hereinbelow, the present invention is specifically described with reference to Examples; however, it is not to be construed as being limited thereto. All publications cited herein are incorporated as part of this description.

Hereinafter, particular administration groups described in the Examples and the Figures related to these Examples have the following compositions.

GMSCF administration group: IMDM supplemented with 10% FBS, which contains recombinant human GM-CSF (100 ng/ml) (Peprotech) and recombinant human stem cell factor (SCF) (50 ng/ml) (Peprotech)

0.1 GMSCF administration group: IMDM supplemented with 10% FBS, which contains recombinant human GM-CSF (10 ng/ml) (Peprotech) and recombinant human stem cell factor (SCF) (5 ng/ml) (Peprotech)

0.01 GMSCF administration group: IMDM supplemented with 10% FBS, which contains recombinant human GM-CSF ng/ml) (Peprotech) and recombinant human stem cell factor (SCF) (0.5 ng/ml) (Peprotech)

GMIL-4 administration group: IMDM supplemented with 10% FBS, which contains recombinant human GM-CSF (100 ng/ml) (Peprotech) and recombinant human IL-4 (50 ng/ml) (Wako, Japan)

IL-3 administration group: IMDM supplemented with 10% FBS, which contains IL-3 (10 ng/ml) (R&D Systems Inc.)

IL-3SCF administration group: IMDM supplemented with 10% FBS, which contains IL-3 (10 ng/ml) (R&D Systems Inc.) and recombinant human SCF (50 ng/ml) (Peprotech)

TPOSCF administration group: IMDM supplemented with 10% FBS, which contains recombinant human TPO (50 ng/ml) (Wako, Japan) and recombinant human SCF (50 ng/ml) (Peprotech)

FS administration group: IMDM supplemented with 10% FBS, which contains recombinant human Flt3-L (100 ng/ml) (Richter-HELM BioLogics GmbH & Co. KG) and recombinant human SCF (50 ng/ml) (Peprotech)

FST6 administration group: IMDM supplemented with 10% FBS, which contains recombinant human Flt3-L (100 ng/ml) (Richter-HELM BioLogics GmbH & Co. KG), recombinant human SCF (50 ng/ml) (Peprotech), recombinant human TPO (50 ng/ml) (Wako, Japan), and recombinant human IL-6 (25 ng/ml)

SCF administration group: IMDM supplemented with 10% FBS, which contains recombinant human SCF (50 ng/ml) (Peprotech)

Hereinafter, (1) iDC treatment and (2) OK432 treatment, which are described in the Figures related to the Examples, refer to the following treatments:

(1) iDC treatment: two days of incubation in the following medium: IMDM supplemented with 10% FBS (2) OK432 treatment: two days of incubation in the following medium: IMDM supplemented with 10% FBS and containing OK432 (0.5 KE/ml) (Chugai Pharmaceutical Co.; Japan Standard Commodity Classification No. 874299)

Unless otherwise specified, cells were cultured at 37° C. under 5% $CO_2$, and the culture medium used was IMDM supplemented with 10% FBS.

Example 1

Figure 2:
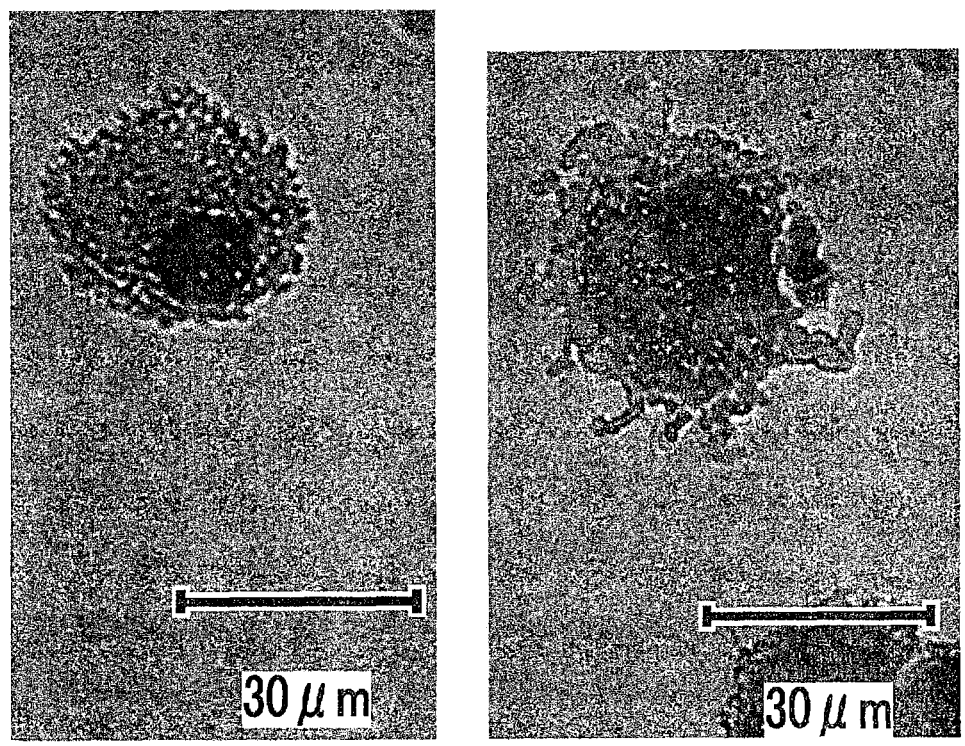
FIG. 2 depicts photographs showing the result of assessing the presence or absence of dendrites when "CD34$^+$ cells are cultured for 28 days under GMSCF administration group culture conditions, followed by seven days of culture under GMIL-4 administration group culture conditions". In this figure, "iDC treatment" indicates a photograph of the cells after iDC treatment, while "OK432 treatment" indicates a photograph of the cells after OK432 treatment. After the "OK432 treatment", dendritic cells showed dendrites. In the photographs of this figure, dendrites are observed in the OK432 treatment group, while none is seen in the iDC treatment group. Thus, "CD34$^+$ cells cultured under GMSCF administration group culture conditions for 28 days, followed by seven days of culture under GMIL-4 administration group culture conditions" are assumed to be dendritic cells.

Preparation of Dendritic Cells from Human-Derived Dendritic Cell Precursor Cells Using Particular Cytokines Human cord blood-derived CD34$^+$ cells (purchased from Lonza) were expanded and differentiated by culturing for 35 days in a medium containing particular cytokine(s). The result of FIG. 1 shows that a large amount of cells were obtained by the method of culturing human cord blood-derived CD34$^+$ cells as the GMSCF administration group for a predetermined period, followed by culture as the GMIL-4 administration group (FIG. 1; indicated as "GMSCF→GMIL-4"). Cell morphology observations revealed that the cells had dendrites after OK432 treatment, which is a dendritic cell activation treatment (FIG. 2). The large population of cells prepared by the method described above is expected to be dendritic cells. As shown in FIG. 1, when compared to the culture method in which culturing is done for particular period under GMSCF administration group culture conditions, followed by GMIL-4 administration group culture conditions, the following methods could yield a large amount of cells, although some of them yielded a smaller number of cells than the others: the method of culturing for a particular period under IL-3SCF administration group culture conditions, followed by culturing under GMIL-4 administration group culture conditions; the method of culturing for a particular period under TPOSCF administration group culture conditions, followed by culturing under GMIL-4 administration group culture conditions; the method of culturing for a particular period under FS administration group culture conditions, followed by culturing under GMIL-4 administration group culture conditions; and the method of culturing for a particular period under FST6 administration group culture conditions, followed by culturing under GMIL-4 administration group culture conditions (FIG. 1; indicated as "SCFIL-3→GMIL-4", "TPO/SCF→GMIL-4", "Flt3-L/SCF→GMIL-4", and "FST6→GMIL-4").

Another experiment, which is not shown in FIG. 1, was also conducted, where the above-described human cord blood-derived CD34$^+$ cells were cultured under SCF administration group culture conditions. Cell expansion was observed during the first week after the start of culture (the cell count at the start of culture was $1.0 \times 10^5$ (cells), while it was about $2.25 \times 10^5$ (cells) one week after). However, after the first week, the cell count decreased due to absence of cell expansion.

Example 2

Determination of IL-12 Production Level in Dendritic Cells Prepared Using Particular Cytokines Dendritic cells prepared from human cord blood-derived CD34$^+$ cells using particular cytokines were assessed for their ability to produce IL-12. Human Inflammation Kit (catalog NO. 551811) from Beckton Dickinson and company (BD) was used in this experiment (FIG. 3).

The OK432 stimulation augmented the IL-12 productivity in all administration groups. However, the results shown in FIGS. 3(A) and (B) demonstrate that the samples of (3) to (7) in FIG. 3 were more competent to produce IL-12 as compared to other samples (excluding the control sample of (8) in FIG. 3).

Example 3

Preparation of Dendritic Cells from Human Peripheral Blood CD14$^+$ Precursor (Monocyte) Using Particular Cytokines Human peripheral blood CD14$^+$ precursor cells (monocytes) were expanded and differentiated via 28 days of culture in a medium containing particular cytokine(s).

Figure 6:
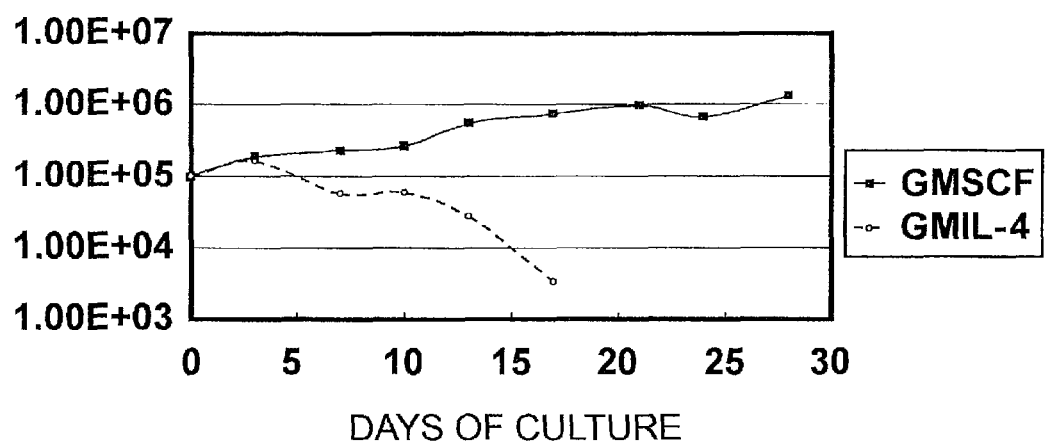
FIG. 6 is a curve graph showing the results of expansion and differentiation when human peripheral blood CD14+ precursor (monocyte) are cultured in a medium containing particular cytokines. The details are described below: "GMSCF": 25-day monocytes culture under GMSCF administration group culture conditions. "GMIL-4": culture of monocytes under GMIL-4 administration group culture conditions. This method is a known culture method (JP-A (Kohyo) 2008-5151439).

The result shown in FIG. 6 suggests that the method using a culture medium containing GM-CSF and SCF is more appropriate to prepare a large amount of dendritic cells from monocytes as compared to the conventional method using a culture medium containing GM-CSF and IL-4.

INDUSTRIAL APPLICABILITY

The present invention enables production of large quantities of dendritic cells. The produced DCs can be made to present cancer antigens for use as anti-tumor DC vaccines. By using the methods of the present invention, it has become possible to efficiently produce a large quantity of DCs even when the number of DC precursor cells obtained from a patient is small. DCs obtained by these production methods have a strong anti-tumor effect, and thus can be used as DC vaccines which are useful in immunotherapy for cancer, infections, and the like. The present invention is expected to contribute greatly to immunotherapy against cancer.

The present invention is not limited to the methods described in the above Examples. The present invention also encompasses various modified embodiments that can readily be conceived by those skilled in the art without departing from descriptions provided in the appended Claims.

The above Examples specifically describe an example of methods for preparing a large amount of dendritic cells having the ability to produce IL-12, which is based on "four weeks of culturing CD34$^+$ cells under GMSCF administration group culture conditions, followed by one week of culture under GMIL-4 administration group culture conditions". Meanwhile, alternative methods are also available, including, for example, the method described below. This is due to the following fact.

The alternative method refers to a method in which "CD34$^+$ cells are cultured for a predetermined period in a particular medium, followed by one week of culture under GMIL-4 administration group culture conditions".

Herein, the "particular medium" refers to a "medium containing GM-CSF at 1 ng/ml or a higher concentration and SCF at 0.5 ng/ml or a higher concentration".

Figure 4:
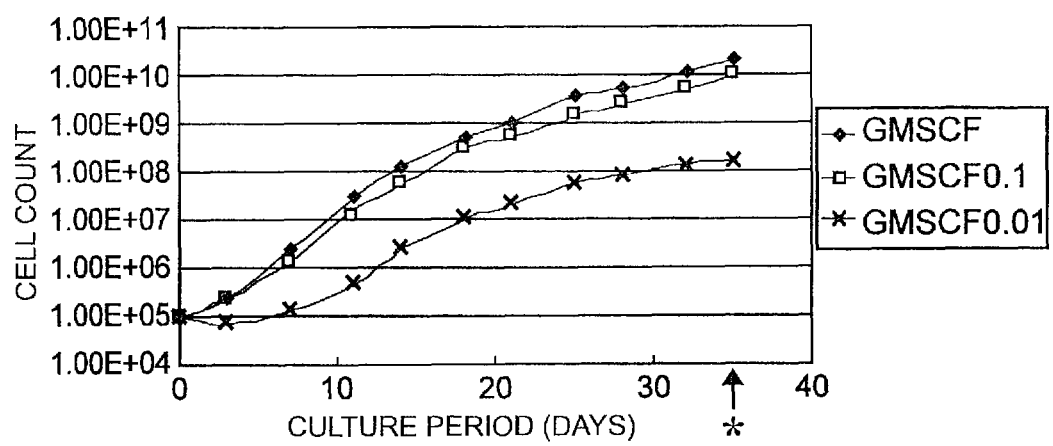
FIG. 4 is a curve graph showing the results of expansion and differentiation when human cord blood-derived CD34+ cells are cultured under the conditions of (1) to (3) below. (1): Culture under GMSCF administration group culture conditions (indicated as "GMSCF" in this figure). (2): Culture under 0.1 GMSCF administration group culture conditions (indicated as "GMSCF0.1" in this figure). (3): Culture under 0.01 GMSCF administration group culture conditions (indicated as "GMSCF0.01" in this figure).
Figure 5:
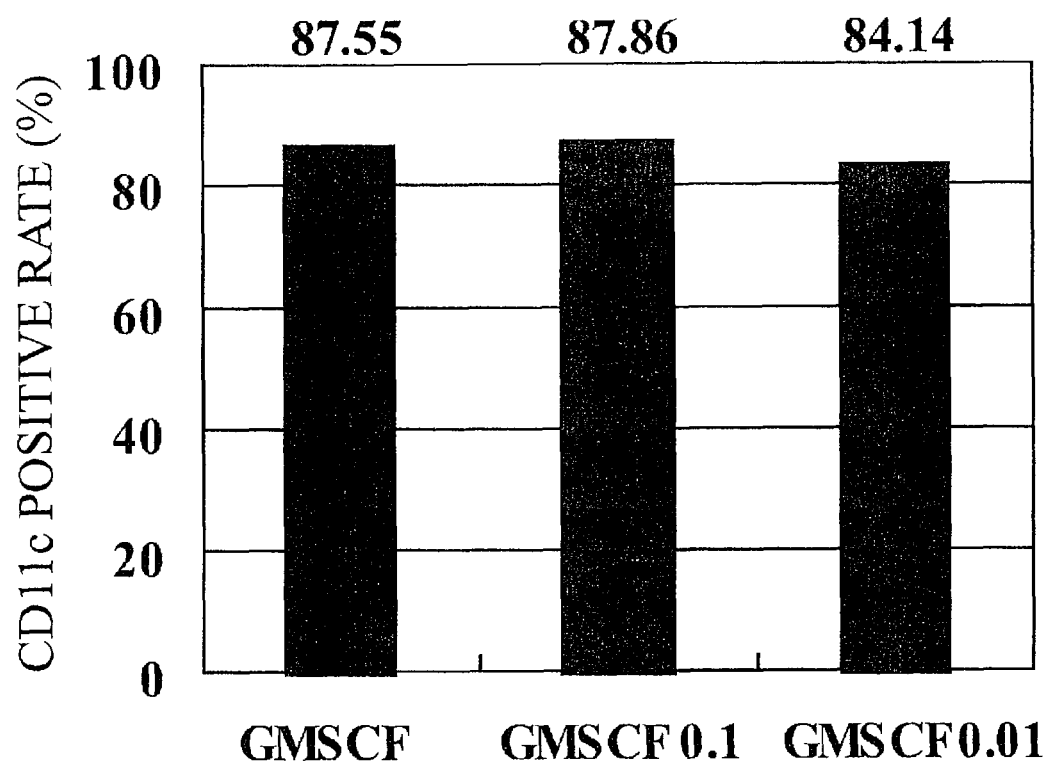
FIG. 5 shows assay results (percentage) for CD11c-positive cells in the cells cultured under each of the conditions at the time point indicated with the asterisk (*) in FIG. 4 described above (i.e., at day 35 of culture). The abbreviations in this figure are as follows. GMSCF: Culture under GMSCF administration group culture conditions. GMSCF0.1: Culture under 0.1 GMSCF administration group culture conditions. GMSCF0.01: Culture under 0.01 GMSCF administration group culture conditions.

The "following fact" refers to the fact that even when the concentrations of GM-CSF (100 ng/ml) and SCF (50 ng/ml) were reduced to $\frac{1}{10}$ (10 ng/ml GM-CSF and 5 ng/ml SCF), a high proliferation was maintained despite a slight reduction in cell count, and furthermore, DC expansion could be achieved even when the concentrations of GM-CSF (100 ng/ml) and SCF (50 ng/ml) were decreased to $\frac{1}{100}$ (1 ng/ml GM-CSF and 0.5 ng/ml SCF) (FIG. 4). The percentage of CD11c-positive cells at day 35 of culture is shown in FIG. 5. There is also the fact that all of the administration groups yielded a high percentage of CD11c-positive cells (FIG. 5).

The invention claimed is:

1. A method for producing a dendritic cell, which comprises culturing a CD34$^+$ or CD14$^+$ dendritic cell precursor, wherein said culturing consists of:
   (1) culturing said CD34$^+$ or CD14$^+$ dendritic cell precursor in the presence of 1 to 500 ng/ml of granulocyte/macrophage-colony stimulating factor (GM-CSF) and 0.5 to 50 ng/ml of stem cell factor (SCF) for 2 to 5 weeks; and
   (2) culturing the cell cultured in step (1) in the presence of 1 to 500 ng/ml of GM-CSF and 0.5 to 50 ng/ml of IL-4 for 3 to 14 days.

2. The method of claim 1, wherein the dendritic cell precursor is a human cell.

3. The method of claim 2, wherein the human cell is a cord blood CD34$^+$ cell.

4. The method of claim 1, wherein the cell is cultured for 3 to 4 weeks in step (1).

5. The method of claim 1, wherein, at the start of step (1), the CD34$^+$ or CD14$^+$ dendritic cell precursor is present at a concentration below of about $1 \times 10^5$ to $2 \times 10^6$ cells/ml.

* * * * *

UNITED STATES PATENT AND TRADEMARK OFFICE
CERTIFICATE OF CORRECTION

PATENT NO. : 8,741,639 B2  
APPLICATION NO. : 13/127753  
DATED : June 3, 2014  
INVENTOR(S) : Yoshikazu Yonemitsu, Yasuji Ueda and Yui Harada Page 1 of 1

It is certified that error appears in the above-identified patent and that said Letters Patent is hereby corrected as shown below:

In the Claims:

Column 26, Claim 5, Line 62, replace "concentration below of" with --concentration of--.

Signed and Sealed this  
Fourteenth Day of October, 2014

Michelle K. Lee  
*Deputy Director of the United States Patent and Trademark Office*